United States Patent
Ebner et al.

(10) Patent No.: US 6,683,161 B1
(45) Date of Patent: Jan. 27, 2004

(54) HUMAN EPENDYMIN

(75) Inventors: Reinhard Ebner, Gaithersburg, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/187,904

(22) Filed: Jul. 3, 2002

Related U.S. Application Data

(62) Division of application No. 09/229,583, filed on Jan. 13, 1999, now Pat. No. 6,489,138.
(60) Provisional application No. 60/075,278, filed on Feb. 19, 1998, and provisional application No. 60/071,330, filed on Jan. 14, 1998.

(51) Int. Cl.[7] .......................... C07K 1/00; C07K 14/00; A61K 38/16; C12P 21/04
(52) U.S. Cl. ....................... 530/395; 530/350; 530/857; 514/8; 435/69.1; 435/70.1
(58) Field of Search ................................. 530/350, 395, 530/857, 326, 327, 328; 514/8, 12, 13, 15; 435/69.1, 70.1

(56) References Cited

U.S. PATENT DOCUMENTS 5,545,719 A 8/1996 Shashoua et al.

FOREIGN PATENT DOCUMENTS

WO    WO 98/11130    3/1998

OTHER PUBLICATIONS

Ogi et al., "Human ependymin–like protein" Nov. 6, 1998, Database : A_Geneseq_101002, Accession No: AAW51119, alignment SEQ ID No: 2 (1–224).*
Ogi et al., "Human ependymin–like protein" Nov. 6, 1998, Database : A_Geneseq_101002, Accession No: AAW51119, alignment SEQ ID No: 2 (2–224).*
Ogi et al., "Human ependymin–like protein" Nov. 6, 1998, Database : A_Geneseq_101002, Accession No: AAW51119, alignment SEQ ID No: 2 (38–224).*
Ogi et al., "Human ependymin–like protein" Nov. 6, 1998, Database : A_Geneseq_101002, Accession No: AAW51119, alignment SEQ ID No: 2 (41–224).*
Ogi et al., "Human ependymin–like protein" Nov. 6, 1998, Database : A_Geneseq_101002, Accession No: AAW51119, alignment SEQ ID No: 2 (1–174).*
Ogi et al., "Human ependymin–like protein" Nov. 6, 1998, Database : A_Geneseq_101002, Accession No: AAW51119, alignment SEQ ID No: 2 (41–174).*
Ogi et al., "Human ependymin–like protein" Nov. 6, 1998, Database : A_Geneseq_101002, Accession No: AAW51119, alignment SEQ ID No: 2 (1–9).*
Ogi et al., "Human ependymin–like protein" Nov. 6, 1998, Database : A_Geneseq_101002, Accession No: AAW51119, alignment SEQ ID No: 2 (8–16).*
Ogi et al., "Human ependymin–like protein" Nov. 6, 1998, Database : A_Geneseq_101002, Accession No: AAW51119, alignment SEQ ID No: 2 (19–27).*

(List continued on next page.)

*Primary Examiner*—Christopher S. F. Low
*Assistant Examiner*—Rita Mitra
(74) *Attorney, Agent, or Firm*—Human Genome Sciences, Inc.

(57) ABSTRACT

The present invention relates to a novel human Ependymin protein which is a member of the ependymin family. In particular, isolated nucleic acid molecules are provided encoding the human Ependymin protein. Ependymin polypeptides are also provided as are vectors, host cells and recombinant methods for producing the same. The invention further relates to screening methods for identifying agonists and antagonists of Ependymin activity. Also provided are diagnostic methods for detecting nervous system-related disorders and therapeutic methods for treating nervous system-related disorders.

91 Claims, 7 Drawing Sheets

OTHER PUBLICATIONS

Ogi et al., "Human ependymin–like protein" Nov. 6, 1998, Database : A_Geneseq_101002, Accession No: AAW51119, alignment SEQ ID No: 2 (69–77).*

Ogi et al., "Human ependymin–like protein" Nov. 6, 1998, Database : A_Geneseq_101002, Accession No: AAW51119, alignment SEQ ID No: 2 (86–107).*

Ogi et al., "Human ependymin–like protein" Nov. 6, 1998, Database : A_Geneseq_101002, Accession No: AAW51119, alignment SEQ ID No: 2 (113–123).*

Ogi et al., "Human ependymin–like protein" Nov. 6, 1998, Database : A_Geneseq_101002, Accession No: AAW51119, alignment SEQ ID No: 2 (131–139).*

Ogi et al., "Human ependymin–like protein" Nov. 6, 1998, Database : A_Geneseq_101002, Accession No: AAW51119, alignment SEQ ID No: 2 (131–139).*

Ogi et al., "Human ependymin–like protein" Nov. 6, 1998, Database : A_Geneseq_101002, Accession No: AAW51119, alignment SEQ ID No: 2 (159–167).*

Genbank Accession No. W58478 (Hillier et al.) (Oct. 15, 1996).

Genbank Accession No. AA209496, Hillier et al. (Jan. 29, 1997).

Genbank Accession No. AA325686 Adams et al. (Apr. 20, 1997).

Genbank Accession No. W58404, Hillier et al. (Oct. 15, 1996).

Genbank Accession No. AA157807, Hillier et al. (Dec. 16, 1996).

Genbank Accession No. AA131847, Hillier et al., (Nov. 27, 1996).

Genbank Accession No. AA442737, Hilliler et al. (Jun. 3, 1997).

Genbank Accession No. N47444, Hillier et al. (Feb. 14, 1996).

Genbank Accession No. N53580, Hillier et al. (Jan. 28, 1997).

Genbank Accession No. AA420449, (Oct. 16, 1997).

Genbank Accession No. C04855, Tanaka et al. (Jul. 30, 1996).

Genbank Accession No. AA131797, Hillier et al. (Nov. 27, 1996).

Genbank Accession No. N49194, Hillier et al. (Feb. 14, 1996).

Genbank Accession No. N50249, Hillier et al. (Feb. 14, 1996).

Genbank Accession No. N47445, Hillier et al. (Feb. 14, 1996).

Genbank Accession No. A659548, (Nov. 5, 1997).

Genbank Accession No. AA322665, Adams et al., (Apr. 14, 1997).

Genbank Accession No. F05414, Auffray et al., (Feb. 19, 1995).

Genbank Accession No. W02349, Hillier et al., (Apr. 18, 1996).

Ogi et al., "Human ependymin–like protein encoding Cdna" Sequence homology search in Geneseq Database, Accession No. V07200, Nov. 6, 1998.

Adams et al. "Initial assessment of human gene diversity and expression patterns based upon 83 million nucleotides of cDNA sequence." Nature 377 (Supp. 6547):3–17 (1995).

Hoffmann, W. "Ependymins and their potential role in nuroplasticity and regeneration: calcium–binding meningeal glycoproteins of the cerebrospinal fluid and extracellular matrix." Int. J. Biochem. (26)5:607–619 (1994).

* cited by examiner

Figure 1A
Human Ependymin

```
  1  CCACGCGTCCGGAAAACCGAAGCGGCAGAAGGCAGTGGCAGCAGCCAGTGGCCCAGGCAG    60

61  AAATAGCTCCCGCGCGATTCACTGGAGCCTTCCCCGGGCCCTGGTCCCGGCTACCGGGAC   120

121  TCGCGCGTCCGGATCTCAAAAGCGGCAGAGGCCACCGAAGGGACAGGAAGCACTTTGGTC   180

181  CAGACCACACTCCCGGCACAGTGCGGAAAGAGCCGGCGGGAGCCACTCTGATCCCGGACG   240

241  CCTCAGCGCCCCCTTGGGCTTGGGCTTGCCCTCGGGCCGGGGAAGGCTGACCGCGATGCC   300
  1                                                            M  P    2

301  AGGACGCGCTCCCCTCCGCACCGTCCCGGGCGCCCTGGGTGCCTGGCTGCTGGGCGGCCT   360
  3   G  R  A  P  L  R  T  V  P  G  A  L  G  A  W  L  L  G  G  L    22
                                                     CD-I

361  CTGGGCCTGGACCCTGTGCGGCCTGTGCAGCCTGGGGGCGGTGGGAGCCCCGCGCCCGTG   420
 23   W  A  W  T  L  C  G  L  C  S  L  G  A  V  G  A  P  R  P  C    42
         CD-I                                           CD-II

421  CCAGGCGCCGCAGCAGTGGGAGGGGCGCCAGGTTATGTACCAGCAAAGTAGCGGGCGCAA   480
 43   Q  A  P  Q  Q  W  E  G  R  Q  V  M  Y  Q  Q  S  S  G  R  N    62
         CD-II

481  CAGCCGCGCCCTGCTCTCCTACGACGGGCTCAACCAGCGCGTGCGGGTGCTGGACGAGAG   540
 63   S  R  A  L  L  S  Y  D  G  L  N  Q  R  V  R  V  L  D  E  R    82
                  CD-III

541  GAAGGCGCTGATCCCCTGCAAGAGATTATTTGAATATATTTTGCTGTATAAGGATGGAGT   600
 83   K  A  L  I  P  C  K  R  L  F  E  Y  I  L  L  Y  K  D  G  V   102
                                                          CD-IV

601  GATGTTTCAGATTGACCAAGCCACCAAGCAGTGCTCAAAGATGACCCTGACACAGCCCTG   660
103   M  F  Q  I  D  Q  A  T  K  Q  C  S  K  M  T  L  T  Q  P  W   122
         CD-IV                           CD-V
                          #
661  GGATCCTCTTGACATTCCTCAAAACTCCACCTTTGAAGACCAGTACTCCATTGGGGGCC   720
123   D  P  L  D  I  P  Q  N  S  T  F  E  D  Q  Y  S  I  G  G  P   142
            CD-VI

721  TCAGGAGCAGATCACCGTCCAGGAGTGGTCGGACAGAAAGTCAGCTAGATCCTATGAAAC   780
143   Q  E  Q  I  T  V  Q  E  W  S  D  R  K  S  A  R  S  Y  E  T   162
            CD-VII
                                                              #.
781  CTGGATTGGCATCTATACAGTCAAGGATTGCTATCCTGTCCAGGAAACCTTTACCATAAA   840
163   W  I  G  I  Y  T  V  K  D  C  Y  P  V  Q  E  T  F  T  I  N   182
            CD-VIII

841  CTACAGTGTGATATTGTCTACGCGGTTTTTTGACATCCAGCTGGGTATTAAAGACCCCTC   900
183   Y  S  V  I  L  S  T  R  F  F  D  I  Q  L  G  I  K  D  P  S   202
                  CD-IX                                CD-X
```

Figure 1B
Human Ependymin

```
 901  GGTGTTTACCCCTCCAAGCACGTGCCAGATGGCCCAACTGGAGAAGATGAGCGAAGACTG   960
 203   V  F  T  P  P  S  T  C  Q  M  A  Q  L  E  K  M  S  E  D  C  222
                         CD-X

961  CTCCTGGTGAGCCTGTGCATAGGGAAGCGGCAGCATCGGATGTCAGCCCCTGCGGCCCC  1020
 223   S  W                                                         224

1021  AGCTGGAGATGGATATGAGACTAGTCAAGATGTGAATGCTAATTGGAGAGAAATATAATT  1080

1081  TTAGGAAGATGCACATTGATGTGGGGTTTTGATGTGTCTGATTTTGACTACTCAAGCTCT  1140

1141  GTTTACAGAAGAAAATTGAATGGCGAGGGTGTGGCCATATGAACTGACTAGATGGCTAAT  1200

1201  ATGGACACTTTGGGTATTTCTAATGCCTGTTCAGCGCTGGTTTTCTGCATGCACGGGTAT  1260

1261  ACACATAATGCAGTGCCATGCACATAGGGAAGGGTCAGTAAGAGAAGTTTGCCTTGGCAG  1320

1321  CAAGTATTTATTGTTGACATTATTCAGAATTAGTGATAATAAAAAGCAGAGTGATTTTGG  1380

1381  TCAATTTTATTATTAATTCTTAAATTCCCTGCAGAGAATGCCCCCTTTATTGCTGCACCA  1440

1441  GGGTGGGCATTGCTCCCACTGAGCCCTACTCCACCCTGTCCCTGCACTCCCTTGGTTGCC  1500

1501  AAAAAATGATAACTTAAATCCCTTCCAGACTTAAGAATTTTATGGCATGGCCCAATTGA  1560

1561  TATAAACATTTAGAAGGAAATGAAAAGCTAAAATAGGAAGTAATTATTCCTCTAAAGAAA  1620

1621  CATTTTGAGCAAGGCAGTTTAGAGAATCCTAATGTCTACACTGGCATAGCACGAGCCATG  1680

1681  TAAGCTTCTTTTTTTTCTATGCAAGAGTATTGATGTATGTGCTGAATCTTCACAGACTTG  1740

1741  TCAATACACAGGCAGTATTCTAAAATAGCACTGAACAGGGAGTCAGGAGACTATTGTCTC  1800

1801  CTAAACCCAGGACTAGAGTTCCCTCGTACTGTCACTCCTTTGGTCATTAAATGCACTGGG  1860

1861  CTTGCCCGCACTTTGGCCTTCCTAGAACGCTGCTTCATAACCTCTCTGTCTGACTTCTGC  1920

1921  ATCTCCTTCCAGGTCAGCTCATTCACAAGAGTTGCTCCCAAGCCTGGATGAGTTGCACCT  1980
```

Figure 1C
Human Ependymin

```
1981  TGCATCTTGAGCATGCATTTCTCACAATAATTATTAAGCTGTGTGATAATTTCTGCTTTC  2040

2041  ACGACACTCATCCATTATCTTGGCTGTGAGCTCCTTGGGTACGGGTACCTTGTATGTTTA  2100

2101  ATTTTATATCCCTAGCACAAAGCAAGTGCCTGGCACATAGTCAGTGCCCTAAGTATTTGT  2160

2161  AGAGTGAAGAATGCCAGCCTCTCTTGTCCCTGGTTTCCTTATGTGTTGAATGTGGTTGAG  2220

2221  TTTGTCCATTGCTAGGGAGAGACTTCCAGTAATAAAATTTACTATTCTAGATGCTTCTAC  2280

2281  TGTTATGTTTTATCTGCCCATTTATCTTTCTTAGTTACCAGGAGAAATGTGTGACACCTA  2340

2341  TATTATAATGAAAACAATCTTATTACTTATAGTTTATCTATATTAAACAAATTTAATTGC  2400

2401  ATTTAAAGCATTCTTTGATATTGTTGCTTTTGCAATAAATATGGATAATCTTGGTTATAA  2460

2461  GGGAGTTAAAACAATGCTGTAATAAATAAAGTGTTTCATGTGATCAAAAAAAAAAAAAA  2520

2521  AAAAA  2525
```

Figure 2

Human Ependymin vs. Zebrafish Ependymin

Percent Similarity: 36.813   Percent Identity: 22.527

```
 40 RPCQAPQQWEGRQVMYQQSSGRNSRALLSYDGLNQRVRVLDERKALIPCK  89
    .||.||       .                  |||     :|  .::
 27 QPCHSPQLTSGTMKVVSTGGHDLASGEFSYDSKTNKFRFVEDTTHANKTS  76

90 RLFEYILLYKDGVMFQIDQATKQCSKMTLTQPWDPLDIPQNSTFEDQYSI 139
    :  :  ::  .:||:::||    .|| ||    ::|!  ..| |  .
 77 YI.DVLIHFEEGVLYEIDSKNESCKKETLQFRKHLMEIPVDATHESESYM 125

140 GGP...QEQITVQEWSDRKSARSYETWIGIYTVKDCYPVQETFTINYSVI 186
    ||     :: : |. |.  |   :  :    |   |   |   .:
126 GSPSLTEQGLRVRVWNG.KFPELHAHYSLSTTSCGCLTVSGSY.YGEKKD 173

187 LSTRFFDIQLGIKDPSVFTPPSTCQMAQLEKMSEDCSW 224
    |  ||  ::  : |  || ||.|:    |.  :| |.
174 LFFSFFGVETEVDDLQVFAPPAYCEGVSFEEAPDDHSF 211
```

Figure 3A

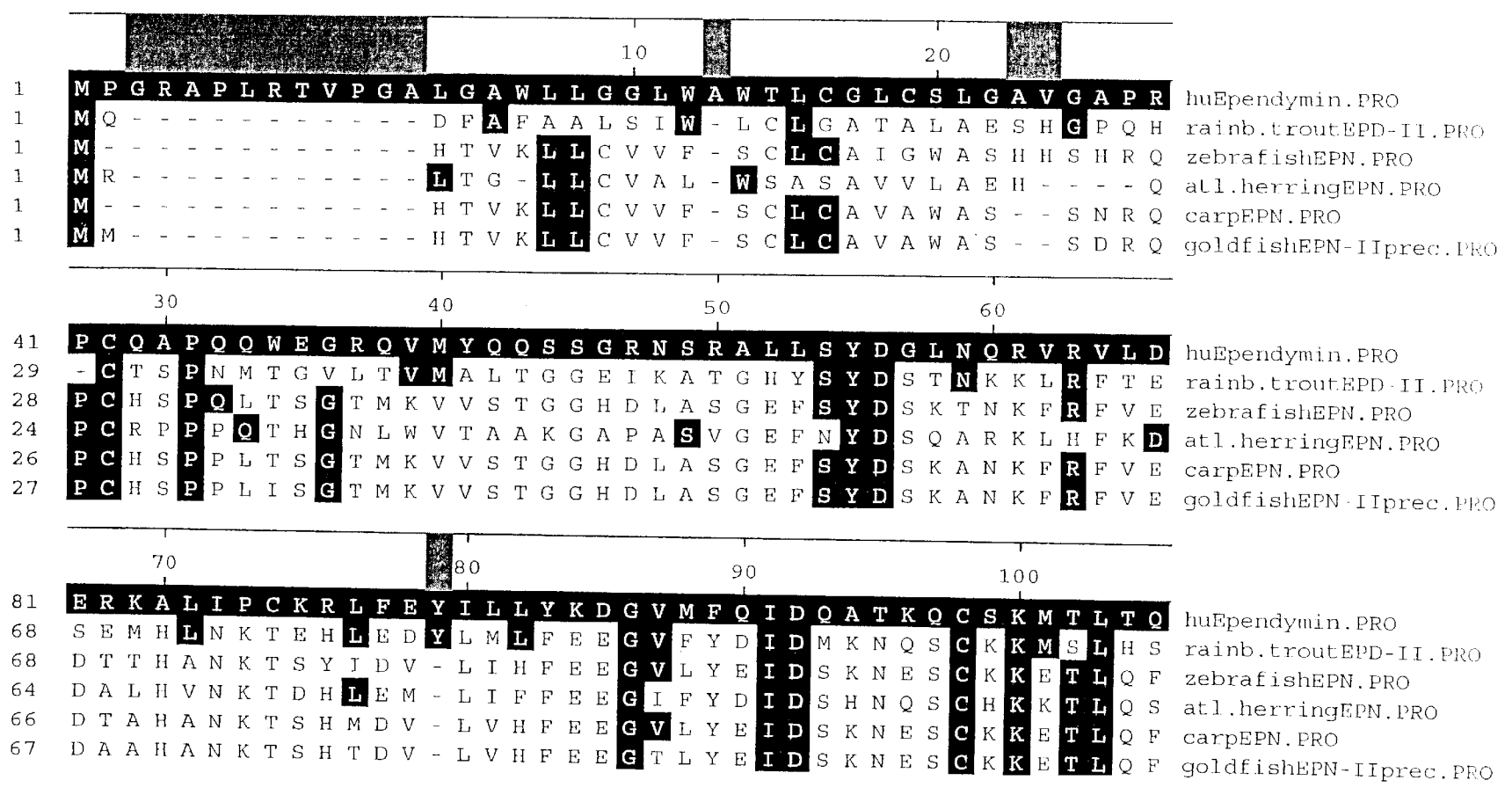

[Sequence alignment figure showing multiple protein sequences: huEpendymin.PRO, rainb.troutEPD-II.PRO, zebrafishEPN.PRO, atl.herringEPN.PRO, carpEPN.PRO, goldfishEPN-IIprec.PRO]

Figure 3B

```
        110                  120                  130                  140
121  P W D P L D I P Q N S T F E D Q Y S I G G P - - Q E Q I T V Q E W S D R K S A   huEpendymin.PRO
108  H A H A L E L P A G A A H Q V E L F L G S D T V Q E D N I K V N I W M G S V A E rainb.troutEPD-II.PRO
107  R K H L M E I P V D A T H E S E S Y M G S P S L T E Q G L R V R V W N G K F P E zebrafishEPN.PRO
103  T Y H C L E V P P N A T H V T E G Y L G S E F I G D Q G V R M R K W R K R V P E atl.herringEPN.PRO
105  R K H L M E I P P D A T H E S E I Y M G S P S I T E Q G L R V W N G K L P E     carpEPN.PRO
106  R K H L M E I P P D A T H E S E I Y M G S P S I T E Q G L R V R V W S G K L P E goldfishEPN-IIprec.PRO 150                  160                  170                  180
158  R S Y E T W I G I Y T V K D C Y P V Q E T F T I N Y S V I L S T R F F D I Q L G huEpendymin.PRO
148  T K G Q Y S A L T - T V G E C L P L S - T F Y S T D S I T L L F S N S E V V T E rainb.troutEPD-II.PRO
147  L H A H Y S L S T - T S C G C L T V S G S Y Y G E K K D L F - F S P F F G V E T E zebrafishEPN.PRO
143  L D G V V T V A T - T S C G C V T L F A T L F T D S N D V L - V F N F L D V E M K atl.herringEPN.PRO
145  L H A H Y S L S T - T S C G C L P V S G S Y Y G D K K D L L - I F S F F G V E T E carpEPN.PRO
146  L H A H Y S L S I - T S C G C L P V S G S Y Y G D K K D L L - L F S F F G V E T E goldfishEPN-IIprec.PRO 190                  200                  210
198  I K D P - S V F T P P S T C Q M A Q L E K M S E D C S W                         huEpendymin.PRO
186  V K A P - E M F T L P S F C E A V E L E E T P K G Q K N D F F N I F N T V       rainb.troutEPD-II.PRO
185  V D D - L Q V F A P P A Y C E G V S F E E A P D D H - - S F F F D L F H D       zebrafishEPN.PRO
182  V K N P L E V F V P P S Y C D G V A L E - - E G D - - T F F F G L F H           atl.herringEPN.PRO
183  V D D - P Q V F V P P A Y C E A V A F E E A P D D H - - S F F F D L F H D       carpEPN.PRO
184  V D D - L Q V F V P P A Y C E G V A F E E A P D D H - - S F F F D L F H D       goldfishEPN-IIprec.PRO
```

Protein Analysis of Human Ependymin

HUMAN EPENDYMIN

CROSS REFERENCE TO RELATED APPLICATION

This application is a divisional of and claims priority under 35 U.S.C. §120 to U.S. No. application Ser. No. 09/229,583, filed Jan. 13, 1999, U.S. Pat. No. 6,489,138, which claims benefit under 35 U.S.C. §119(e) of U.S. Provisional Application Ser. No. 60/071,330, filed on Jan. 14, 1998, and U.S. Provisional Application Ser. No. 60/075,278, filed on Feb. 19, 1998, all of which is hereby incorporated by reference in its entirety.

FIELD OF THE INVENTION

The present invention relates to a novel human gene encoding a polypeptide which is a member of the Ependymin family. More specifically, isolated nucleic acid molecules are provided encoding a human polypeptide named Ependymin. Ependymin polypeptides are also provided, as are vectors, host cells and recombinant methods for producing the same. Also provided are diagnostic methods for detecting disorders related to the nervous system, and therapeutic methods for treating such disorders.

The invention further relates to screening methods for identifying agonists and antagonists of Ependymin activity.

BACKGROUND OF THE INVENTION

Within the last several years, a number of ependymins have been molecularly cloned from a variety of teleost fish including *Oncorhynchus mykiss* (rainbow trout; Muller-Schmid, A., et al., *Gene* 118:189–196 (1992)), *Salmo salar* (Atlantic salmon; Muller-Schmid, A., et al., *Gene* 118:189–196 (1992)), *Esox lucius* (pike; Muller-Schmid, A., et al., *J. Molec. Evol.* 36:578–585 (1993)), *Carassius auratus* (goldfish; Konigstorfer, A., et al., *J. Neurochem.* 52:310–312 (1989); Konigstorfer, A., et al., *J. Biol. Chem.* 264:13689–13692 (1989)), *Brachydanio rerio* (zebrafish; Sterrer, S., et al., *Neurosci.* 37:277–284 (1990)), and *Clupea harengus* (herring, Muller-Schmid, et al., *J. Molec. Evol.* 36:578–585 (1993)). The ependymins produced by these organisms are synthesized as precursors which contain N-terminal, hydrophobic signal sequences. Each of these molecules contains multiple N-linked glycosylation sites, only some of which are conserved between species (Schmidt, R. and Shashoua, V. E. *J. Neurochem.* 36:1368–1377 (1981); Schmidt, R. and Shashoua, V. E. *J. Neurochem.* 40:652–660 (1983); Ganb, B. and Hoffman, W. *Eur. J. Biochem.* 217:275–280 (1993)). The precursor ependymins range in apparent molecular mass from 23.7 to 24.5 kDa, while the secreted mature forms of these molecules are typically 21.6–22.3 kDa in size.

The piscine ependymins characterized thus far may be categorized according to the number of cysteine residues present in the mature polypeptide. Mature salmoniform (*O. mykiss, S. salar*, and *E. lucius*) ependymin polypeptides contain only four cysteine residues, whereas mature cypriniform (*C. auratus* and *B. rerio*) and clupeiform (*C. harengus*) ependymin polypeptides contain five and six cysteine residues, respectively (Hoffmann, W. Int. *J. Biochem.* 26:607–619 (1994)). Correspondingly, disulfide-linked dimerization of the salmoniform ependymin polypeptides is not observed after non-reducing SDS-PAGE. However, cypriniform and clupeiforn ependymins are observed as disulfide-linked dimers under non-reducing conditions. It is speculated that the dimerization occurs via the cysteine residue conserved only between the salmoniform ependymins (this cysteine residue aligns with the lysine residue at location 133 of human ependymin of the present invention as shown in SEQ ID NO:2).

Several lines of evidence have provided the basis for an understanding of the functional role(s) of the ependymins. $Ca^{2+}$-binding has been demonstrated for at least goldfish and rainbow trout ependymins (Schmidt, R. and Makiola, *E. Neuro. Chem.(Life Sci. Adv.)* 10:161–171 (1991); Ganb, B. and Hoffman, supra). Further, ependymins are the primary cerebrospinal fluid component in a number of teleost fish (Schmidt, R. and Lapp, *H. Neurochem. Int.* 10:383–390 1987; ). Finally, roughly two-thirds of Ca2+ in the CSF of rainbow trout is protein-bound (Ganb, B. and Hoffmnan, supra). As a result, it is thought that ependymins may function in $Ca^{2+}$ homeostasis of the teleost piscine brain (Hoffman, W., supra).

In situ hybridization analyses have shown that ependymins are apparently synthesized exclusively in miningeal fibroblasts of the mininx (also termed the endomeninx or leptomeninx) of teleost fish (Konigstorfer, A., et al., *Cell Tissue Res.* 261:59–64 (1990)). Ependymins have also been found to associate with collagen fibrils of the extracellular matrix (ECM; Schwarz, H., et al. *Cell Tissue Res.* 273:417–425 (1993)), and, further, have the capacity to serve as a substrate for outgrowing retinal axons (Schmidt, J. T., et al., *J. Neurobiol.* 22:40–54 (1991)).

An additional role for ependymins has been identified in the field of learning and memory. Using an experimental approach in which goldfish learn to swim to a specific compartment of its environment to avoid an electric shock, investigators have determined that the amount of unbound or unincorporated extracellular ependymins decreases after learning (Piront, M. -L., and Schmidt, R. *Brain Res.* 442:53–62 (1988); Schmidt, R. *J. Neurochem.* 48:1870–1878 (1987)). Further, blockage of functional ependymin molecules, either with antibodies or antisense polynucleotides, resulted in the reversible inability of the experimental animal to remember the task which it had learned. Removal of the inhibitory substance then resulted in a reappearance of the learned ability (Schmidt, R. J. supra; Shashoua, V. E. and Moore, M. E. *Brain Res.* 148:441–449. (1978)).

Thus, there is a need for polypeptides that function as neurotrophic factors in the regeneration of the optic and other nerves and in long-term memory consolidation, since disturbances of such regulation may be involved in disorders relating to the complex molecular and cellular process regulating neuronal and nervous system function. Such disorders may include Parkinson's disease, Alzheimer's disease, amyotrophic lateral sclerosis, pain, stroke, depression, anxiety, epilepsy, and other neurological and psychiatric disorders. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the Ependymin polypeptide having the complete amino acid sequence shown in SEQ ID NO:2 or the complete amino acid sequence encoded by the cDNA clone deposited as plasmid DNA as ATCC Deposit Number 209464 on Nov. 14, 1997. The nucleotide sequence determined by sequencing the deposited Ependymin clone, which is shown in FIGS. 1A, 1B, and 1C (SEQ ID NO:1), contains an open reading frame encoding a complete polypeptide of 224 amino acid residues, including an initiation codon encoding an N-terminal methionine at nucleotide positions 296–298, and a predicted molecular weight of about 25.4 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC Deposit Number 209464, which molecules also can encode additional amino acids fused to the N-terminus of the Ependymin amino acid sequence.

The encoded polypeptide has a predicted leader sequence of 37 amino acids underlined in FIGS. 1A, 1B, and 1C; and the amino acid sequence of the predicted mature Ependymin protein is also shown in FIGS. 1A, 1B, and 1C, as amino acid residues 38–224 and as residues 1–187 in SEQ ID NO:2.

Thus, one aspect of the invention provides an isolated nucleic acid molecule comprising a polynucleotide having a nucleotide sequence selected from the group consisting of: (a) a nucleotide sequence encoding the Ependymin polypeptide having the complete amino acid sequence in SEQ ID NO:2 (i.e., positions −37 to 187 of SEQ ID NO:2); (b) a nucleotide sequence encoding the Ependymin polypeptide having the complete amino acid sequence in SEQ ID NO:2 excepting the N-terminal methionine (i.e., positions −36 to 187 of SEQ ID NO:2); (c) a nucleotide sequence encoding the predicted mature Ependymin polypeptide having the amino acid sequence at positions 1 to 187 in SEQ ID NO:2; (d) a nucleotide sequence encoding the Ependymin polypeptide having the complete amino acid sequence encoded by the cDNA clone contained in ATCC Deposit No. 209464; (e) a nucleotide sequence encoding the Ependymin polypeptide having the complete amino acid sequence excepting the N-terminal methionine encoded by the cDNA clone contained in ATCC Deposit No. 209464; (f) a nucleotide sequence encoding the mature Ependymin polypeptide having the amino acid sequence encoded by the cDNA clone contained in ATCC Deposit No. 209464; and (g) a nucleotide sequence complementary to any of the nucleotide sequences in (a), (b), (c), (d), (e) or (f), above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues.

An additional nucleic acid embodiment of the invention relates to an isolated nucleic acid molecule comprising a polynucleotide which encodes the amino acid sequence of an epitope-bearing portion of a Ependymin polypeptide having an amino acid sequence in (a), (b), (c), (d), (e) or (f), above. A further nucleic acid embodiment of the invention relates to an isolated nucleic acid molecule comprising a polynucleotide which encodes the amino acid sequence of a Ependymin polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a polynucleotide which encodes the amino acid sequence of a Ependymin polypeptide to have an amino acid sequence which contains not more than 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of Ependymin polypeptides or peptides by recombinant techniques.

The invention further provides an isolated Ependymin polypeptide comprising an amino acid sequence selected from the group consisting of: (a) the amino acid sequence of the full-length Ependymin polypeptide having the complete amino acid sequence shown in SEQ ID NO:2 (i.e., positions −37 to 187 of SEQ ID NO:2); (b) the amino acid sequence of the full-length Ependymin polypeptide having the complete amino acid sequence shown in SEQ ID NO:2 excepting the N-terminal methionine (i.e., positions −36 to 187 of SEQ ID NO:2); (c) the amino acid sequence of the predicted mature Ependymin polypeptide having the amino acid sequence at positions 1 to 187 in SEQ ID NO:2; (d) the complete amino acid sequence encoded by the cDNA clone contained in the ATCC Deposit No. 209464; (e) the complete amino acid sequence excepting the N-terminal methionine encoded by the cDNA clone contained in the ATCC Deposit No. 209464; and (f) the complete amino acid sequence of the predicted mature Ependymin polypeptide encoded by the cDNA clone contained in the ATCC Deposit No. 209464. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f), above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a Ependymin polypeptide having an amino acid sequence described in (a), (b), (c), (d), (e) or (f), above. Peptides or polypeptides having the amino acid sequence of an epitope-bearing portion of a Ependymin polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a peptide or polypeptide which comprises the amino acid sequence of a Ependymin polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a peptide or polypeptide to have an amino acid sequence which comprises the amino acid sequence of a Ependymin polypeptide, which contains at least one, but not more than 10, 9, 8, 7, 6, 5, 4, 3, 2 or 1 conservative amino acid substitutions.

In another embodiment, the invention provides an isolated antibody that binds specifically to a Ependymin polypeptide having an amino acid sequence described in (a), (b), (c), (d), (e) or (f) above. The invention further provides methods for isolating antibodies that bind specifically to a Ependymin polypeptide having an amino acid sequence as described herein. Such antibodies are useful diagnostically or therapeutically as described below.

The invention also provides for pharmaceutical compositions comprising Ependymin polypeptides, particularly human Ependymin polypeptides, which may be employed, for instance, to treat Parkinson's disease, Alzheimer's disease, amyotrophic lateral sclerosis, pain, stroke, depression, anxiety, epilepsy, and other neurological and psychiatric disorders. Methods of treating individuals in need of Ependymin polypeptides are also provided.

The invention further provides compositions comprising a Ependymin polynucleotide or an Ependymin polypeptide for administration to cells in vitro, to cells ex vivo and to cells in vivo, or to a multicellular organism. In certain particularly preferred embodiments of this aspect of the invention, the compositions comprises a Ependymin polynucleotide for expression of a Ependymin polypeptide in a host organism for treatment of disease. Particularly preferred in this regard is expression in a human patient for treatment of a dysfunction associated with aberrant endogenous activity of a Ependymin In another aspect, a screening assay for agonists and antagonists is provided which involves determining the effect a candidate compound has on Ependymin binding to a receptor. In particular, the method involves contacting the receptor with a Ependymin polypeptide and a candidate compound and determining whether Ependymin polypeptide binding to the receptor is increased or decreased due to the presence of the candidate compound. In this assay, an increase in binding of Ependymin over the standard binding indicates that the candidate compound is an agonist of Ependymin binding activity and a decrease in Ependymin binding compared to the standard indicates that the compound is an antagonist of Ependymin binding activity.

In yet another aspect, the Ependymin may bind to a cell surface protein which also function as a viral receptor or coreceptor. Thus, Ependymin, or agonists or antagonists thereof, may be used to regulate viral infectivity at the level of viral binding or interaction with the Ependymin receptor or coreceptor or during the process of viral internalization or entry into the cell.

It has been discovered that Ependymin is expressed not only in primary dendritic cells, but also in the KMH2 cell line, placenta, fetal and adult liver, spinal cord, osteoclastoma, cerebellum, synovial fibroblasts, 12 week old early stage human embryo, adrenal gland tumor, whole brain, Hodgkin's Lymphoma tissue, macrophages, HEL cell line, and chondrosarcoma. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the nervous system, significantly higher or lower levels of Ependymin gene expression may be detected in certain tissues (e.g., cancerous and wounded tissues) or bodily fluids (e.g., serum, plasma, urine, synovial fluid or spinal fluid) taken from an individual having such a disorder, relative to a "standard" Ependymin gene expression level, i.e., the Ependymin expression level in healthy tissue from an individual not having the nervous system disorder. Thus, the invention provides a diagnostic method useful during diagnosis of such a disorder, which involves: (a) assaying Ependymin gene expression level in cells or body fluid of an individual; (b) comparing the Ependymin gene expression level with a standard Ependymin gene expression level, whereby an increase or decrease in the assayed Ependymin gene expression level compared to the standard expression level is indicative of disorder in the nervous system.

An additional aspect of the invention is related to a method for treating an individual in need of an increased level of Ependymin activity in the body comprising administering to such an individual a composition comprising a therapeutically effective amount of an isolated Ependymin polypeptide of the invention or an agonist thereof.

A still further aspect of the invention is related to a method for treating an individual in need of a decreased level of Ependymin activity in the body comprising, administering to such an individual a composition comprising a therapeutically effective amount of an Ependymin antagonist. Preferred antagonists for use in the present invention are Ependymin-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of Ependymin. The predicted leader sequence of about 37 amino acids is underlined. Note that the methionine residue at the beginning of the leader sequence in FIGS. 1A, 1B, and 1C is shown in position number (positive) 1, whereas the leader positions in the corresponding sequence of SEQ ID NO:2 are designated with negative position numbers. Thus, the leader sequence positions 1 to 37 in FIGS. 1A, 1B, and 1C correspond to positions −37 to −1 in SEQ ID NO:2.

Figure 4:
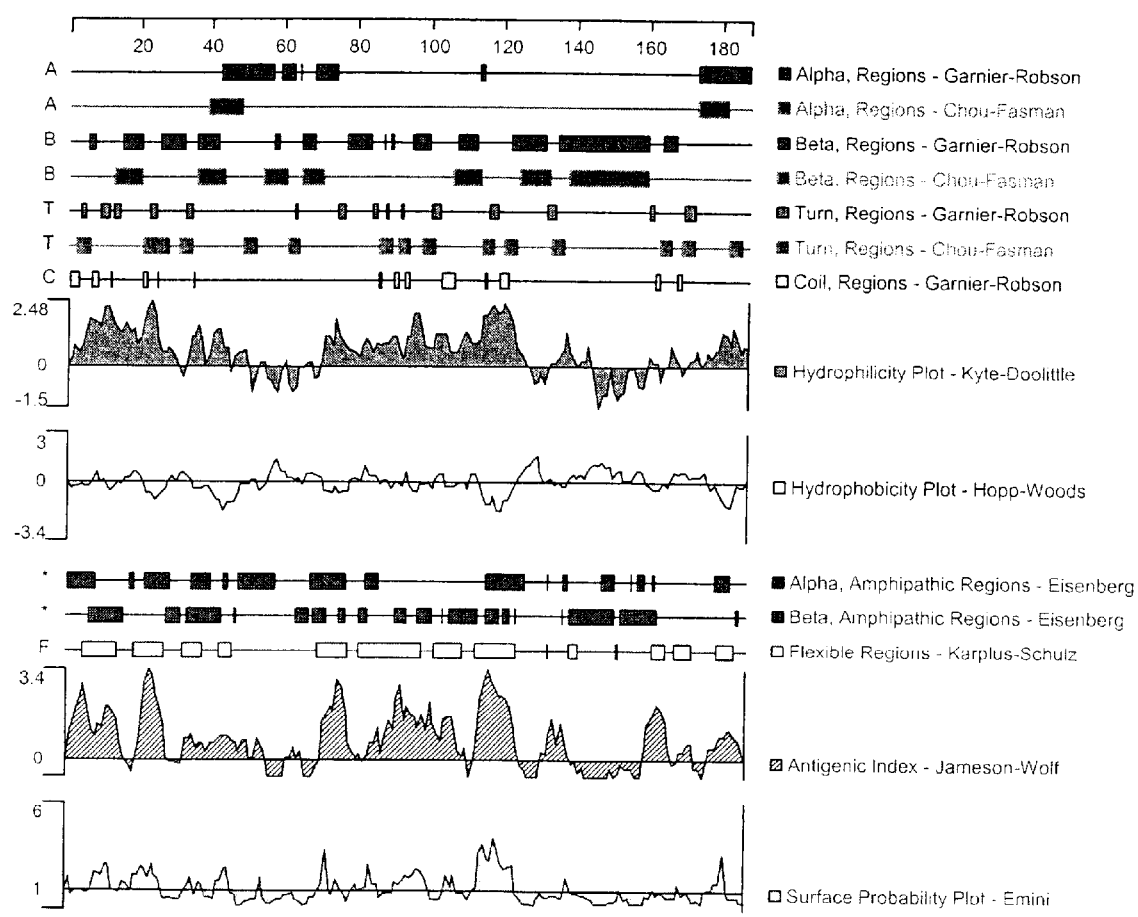

Two potential asparagine-linked glycosylation sites are marked in the amino acid sequence of Ependymin. The sites are asparagine-130 and asparagine-182 in FIGS. 1A, 1B, and 1C (asparagine-93 and asparagine-145 in SEQ ID NO:2), and are labeled with the bold pound symbol (#) above the nucleotide sequence coupled with a bolded one letter abbreviation for the asparagine (N) in the amino acid sequence in FIGS. 1A, 1B, and 1C; that is, the actual asparagine residues which are potentially glycosylated is bolded in FIGS. 1A, 1B, and 1C.

A polyadenylation signal sequence is present in the 3' untranslated region of the nucleotide sequence of Ependymin of the present invention. The polyadenylation signal sequence is delineated by a double underline in the Ependymin sequence shown in FIGS. 1A, 1B, and 1C.

Regions of high identity between Human Ependymin of the present invention and several previously identified piscine ependymins (an alignment of these sequences is presented in FIG. 2) are delineated in FIGS. 1A, 1B, and 1C with a double underline. These regions are not limiting and are labeled as Conserved Domain (CD)-II, CD-E, CD-IV, CD-V, CD-VI, CD-VII, CD-IX, and CD-X in FIGS. 1A, 1B, and 1C.

FIG. 2 shows the regions of identity between the amino acid sequences of the Ependymin protein and translation product of the Zebrafish mRNA for Ependymin (SEQ ID NO:6), determined by the computer program Bestfit (Wisconsin Sequence Analysis Package, Version 8 for Unix, Genetics Computer Group, University Research Park, 575 Science Drive, Madison, Wis. 53711) using the default parameters.

FIGS. 3A and 3B are a multiple sequence alignment illustrating a comparison of the amino acid sequences of the novel human ependymin of the present invention (SEQ ID NO:2) and five previously described ependymin-like molecules. Conserved residues are highlighted in black. The ependymin homologues shown in the figure are goldfish ependymin II (SEQ ID NO:3; GenBank Accession No. J04986), rainbow trout ependymin II (SEQ ID NO:4; GenBank Accession No. M93698), common carp ependymin (SEQ ID NO:5; GenBank Accession No. U00432), zebrafish ependymin (SEQ ID NO:6; GenBank Accession No. X52502), and Atlantic herring ependymin (SEQ ID NO:7; GenBank Accession No. L09065).

FIG. 4 shows an analysis of the Ependyrnin amino acid sequence. Alpha, beta, turn and coil regions; hydrophilicity and hydrophobicity; amphipathic regions; flexible regions; antigenic index and surface probability are shown. In the "Antigenic Index or Jameson-Wolf" graph, the positive peaks indicate locations of the highly antigenic regions of the Ependymin protein, i.e., regions from which epitope-bearing peptides of the invention can be obtained.

The data presented in FIG. 4 are also represented in tabular form in Table I. The columns are labeled with the headings "Res", "Position", and Roman Numerals I–XIV. The column headings refer to the following features of the amino acid sequence presented in FIG. 4 and Table I: "Res": amino acid residue of FIGS. 1A, 1B, and 1C (which is the identical sequence shown in SEQ ID NO:2, with the exception that the residues are numbered 1–224 in FIGS. 1A, 1B, and 1C and −37 through 187 in SEQ ID NO:2); "Position": position of the corresponding residue within FIGS. 1A, 1B, and 1C (which is the identical sequence shown in SEQ ID NO:2, with the exception that the residues are numbered 1–224 in FIGS. 1A, 1B, and 1C and −37 through 187 in SEQ ID NO:2); I: Alpha, Regions—Garnier-Robson; II: Alpha, Regions—Chou-Fasman; In: Beta, Regions—Gamier-Robson; IV: Beta, Regions—Chou-Fasman; V: Turn, Regions—Gamier-Robson; VI: Turn, Regions—Chou-Fasman; VII: Coil, Regions—Gamier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

The present invention provides isolated nucleic acid molecules comprising a polynucleotide encoding a Ependymin polypeptide having the amino acid sequence shown in SEQ ID NO:2, which was determined by sequencing a cloned cDNA. The nucleotide sequence shown in FIGS. 1A, 1B, and 1C (SEQ ID NO:1) was obtained by sequencing the HDPIE88 clone, which was deposited on Nov. 14, 1997 at the American Type Culture Collection, 10801 University Boulevard, Manassas, Va. 20110-2209, and given accession number ATCC 209464. The deposited clone is contained in the pbluescript SK(−) plasmid (Stratagene, La Jolla, Calif.).

The Ependymin protein of the present invention shares sequence homology with the translation products of ependymins from a number of teleost fish including the Zebrafish mRNA for ependymin (FIG. 2; SEQ ID NO:6). Zebrafish ependymin, and other ependymins, are thought to be involved in the regulation of extracellular $Ca^{2+}$-binding. In fact, as the predominant cerebrospinal fluid constituents in many teleost fish, ependymins are believed to be antiadhesive extracellular matrix glycoproteins which function in the processes of cell contact and regeneration.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ID NO:1), a nucleic acid molecule of the present invention encoding a Ependymin polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from primary dendritic cells.

Additional clones of the same gene were also identified in cDNA libraries from the following tissues: the KMH2 cell line, placenta, fetal and adult liver, spinal cord, osteoclastoma, cerebellum, synovial fibroblasts, 12 week old early stage human embryo, adrenal gland tumor, whole brain, Hodgkin's Lymphoma tissue, macrophages, HEL cell line, and chondrosarcoma.

The determined nucleotide sequence of the Ependymin cDNA of FIGS. 1A, 1B, and 1C (SEQ ID NO:1) contains an open reading frame encoding a protein of 224 amino acid residues, with an initiation codon at nucleotide positions 296–298 of the nucleotide sequence in FIGS. 1A, 1B, and 1C (SEQ ID NO:1), and a deduced molecular weight of about 25.4 kDa. The amino acid sequence of the Ependymin protein shown in SEQ ID NO:2 is about 22.5 % identical to Zebrafish mRNA for ependymin (FIG. 2; Sterrer, S., et al., Neurosci. 37:277–284 (1990); GenBank Accession No. X52502).

As one of ordinary skill would appreciate, due to the possibilities of sequencing errors discussed above, the actual complete Ependymin polypeptide encoded by the deposited cDNA, which comprises about 224 amino acids, may be somewhat longer or shorter. It will further be appreciated that, depending on the analytical criteria used for identifying various functional domains, the exact "address" of the signal peptide and mature regions of the Ependymin polypeptide may differ slightly from the predicted positions above. For example, the exact location of the Ependymin signal peptide in SEQ ID NO:2 may vary slightly (e.g., the address may "shift" by about 1 to about 15 residues, more likely about 1 to about 10 residues, and even more likely about 1 to about 5 residues) depending on the criteria used to define the domain. In this case, the end of the signal peptide and the beginning of the mature Ependymin molecule were predicted using the Human Genome Sciences, Inc. (HGSI) SignalP computer algorithm (Pedersen, A. G. and Nielsen, H. *ISMB* 5:226–233 (1997)). One of skill in the art will realize that another widely accepted computer algorithm used to predict potential sites of polypeptide cleavage, PSORT, will predict the cleavage of an N-terminal signal peptide from the Ependymin polypeptide at a point slightly different from that predicted by the HGSI SignalP algorithm. In any event, as discussed further below, the invention further provides polypeptides having various residues deleted from the N-terminus of the complete polypeptide, including polypeptides lacking one or more amino acids from the N-terminus of the mature polypeptide described herein.

Leader and Mature Sequences

The amino acid sequence of the complete Ependymin protein includes a leader sequence and a mature protein, as shown in SEQ ID NO:2. More in particular, the present invention provides nucleic acid molecules encoding a mature form of the Ependymin protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature Ependymin polypeptide having the amino acid sequence encoded by the cDNA clone contained in ATCC Deposit No. 209464. By the "mature Ependymin polypeptide having the amino acid sequence encoded by the cDNA clone in ATCC Deposit No. 209464" is meant the mature form(s) of the Ependymin protein produced by expression in a mammalian cell (e.g., COS cells, as described below) of the complete open reading frame encoded by the human DNA sequence of the deposited clone.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage-points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete Ependymin polypeptide was analyzed by the HGSI SignalP computer algorithm (Pedersen, A. G. and Nielsen, H. *ISMB* 5:226–233 (1997)). Using this computer analysis tool, a likely site of signal peptide cleavage was predicted between amino acid residues 37 and 38 of the Ependymin sequence (SEQ ID NO:2). However, the deduced amino acid sequence of the complete Ependymin polypeptide was also analyzed by a computer program designated "PSORT", available from Dr. Kenta Nakai of the Institute for Chemical Research, Kyoto University (Nakai, K. and Kanehisa, M. *Genomics* 14:897–911 (1992)), which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2.

As one of ordinary skill would appreciate from the above discussions, due to the possibilities of sequencing errors as well as the variability of cleavage sites in different known proteins, the mature Ependymin polypeptide encoded by the deposited cDNA is expected to consist of about 187 amino acids (presumably residues 1 to 187 of SEQ ID NO:2) based on analysis of the Ependymin amino acid sequence using the SignalP computer algorithm, but may consist of any number of amino acids in the range of about 187 to 200 amino acids (the mature polypeptide is predicted to be 200 amino acids using the PSORT computer algorithm). Further, the actual leader sequence(s) of this protein is expected to be 37 amino acids (presumably residues −37 through −1 of SEQ ID NO:2) based on analysis of the Ependymin amino acid sequence using the SignalP computer algorithm, but may consist of any number of amino acids in the range of 24–37 amino acids (the signal peptide is predicted to be 24 amino acids using the PSORT computer algorithm).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 288–290 of the nucleotide sequence shown in FIGS. 1A, 1B, and 1C (SEQ ID NO:1).

Also included are DNA molecules comprising the coding sequence for the predicted mature Ependymin protein shown at positions 1–187 of SEQ ID NO:2.

In addition, isolated nucleic acid molecules of the invention include DNA molecules which comprise a sequence substantially different from those described above but which, due to the degeneracy of the genetic code, still encode the Ependymin protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as E. coli).

In another aspect, the invention provides isolated nucleic acid molecules encoding the Ependymin polypeptide having an amino acid sequence encoded by the cDNA clone contained in the plasmid deposited as ATCC Deposit No. 209464 on Nov. 14, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A, 1B, and 1C (SEQ ID NO:1) or the nucleotide sequence of the Ependymin cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the Ependymin gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–967 of SEQ ID NO:1.

In addition, the invention provides nucleic acid molecules having nucleotide sequences related to extensive portions of SEQ ID NO:1 which have been determined from the following related cDNA clones: HATBS80R (SEQ ID NO:15); HSRAN11R (SEQ ID NO:16); HCECE56R (SEQ ID NO:17); HSNBF20R (SEQ ID NO:18); HPMDJ94R (SEQ ID NO:19); and HE2FK31R (SEQ ID NO:20).

Further, the invention includes a polynucleotide comprising any portion of at least about 30 nucleotides, preferably at least about 50 nucleotides, of SEQ ID NO:1 from residue 1 to 2505.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the Ependymin polypeptide as identified in FIGS. 3A and 3B and described in more detail below.

Preferred nucleic acid fragments of the present invention also include nucleic acid molecules encoding one or more of the following domains of Human Ependymin: amino acid residues −20 through −10 of SEQ ID NO:2; amino acid residues 1 through 10 of SEQ ID NO:2; amino acid residues 31 through 40 of SEQ ID NO:2; amino acid residues 64 through 70 of SEQ ID NO:2; amino acid residues 76 through 82 of SEQ ID NO:2; amino acid residues 88 through 105 of SEQ ID NO:2; amino acid residues 106 through 117 of SEQ ID NO:2; amino acid residues 129 through 143 of SEQ ID NO:2; amino acid residues 150 through 156 of SEQ ID NO:2; and amino acid residues 162 through 184 of SEQ ID NO:2. These domains are represented as conserved domains CD-I through CD-X in FIGS. 1A, 1B, and 1C.

In specific embodiments, the polynucleotide fragments of the invention encode antigenic regions. Non-limiting examples of antigenic polypeptides or peptides that can be used to generate Ependymin-specific antibodies include: a polypeptide comprising amino acid residues from about Ala-1 to about Gln-9 in SEQ ID NO:2; a polypeptide comprising amino acid residues from about Pro-8 to about Val-16 in SEQ ID NO:2; a polypeptide comprising amino acid residues from about Gln-19 to about Arg-27 in SEQ ID NO:2; a polypeptide comprising amino acid residues from about Ile-69 to about Ser-77 in SEQ ID NO:2; a polypeptide comprising amino acid residues from about Asp-86 to about Glu-107 in SEQ ID NO:2; a polypeptide comprising amino acid residues from about Glu-113 to about Tyr-123 in SEQ ID NO:2; a polypeptide comprising amino acid residues from about Thr-131 to about Gln-139 in SEQ ID NO:2; a polypeptide comprising amino acid residues from about Leu-159 to about Phe-167 in SEQ ID NO:2; and a polypeptide comprising amino acid residues from about Leu-178 to about Ser-186 in SEQ ID NO:2.

In additional embodiments, the polynucleotides of the invention encode functional attributes of Human Ependymin. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Human Ependymin.

The data representing the structural or functional attributes of Human Ependymin set forth in FIG. 4 and/or Table I, as described above, was generated using the various modules and algorithms of the DNA*STAR set on default parameters. In a preferred embodiment, the data presented in columns VIII, IX, XIII, and XIV of Table I can be used to determine regions of Human Ependymin which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 4, but may, as shown in Table I, be represented or identified by using tabular representations of the data presented in FIG. 4. The DNA*STAR computer algorithm used to generate FIG. 4 (set on the original default parameters) was used to present the data in FIG. 4 in a tabular format (See Table I). The tabular format of the data in FIG. 4 may be used to easily determine specific boundaries of a preferred region.

The above-mentioned preferred regions set out in FIG. 4 and in Table I include, but are not limited to, regions of the aforementioned types identified by analysis of the amino acid sequence set out in FIGS. 1A, 1B, and 1C. As set out in FIG. 4 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | T | . | 0.31 | −0.24 | * | * | . | 1.07 | 1.11 |
| Pro | 2 | . | . | . | . | . | T | C | 0.49 | −0.17 | . | * | . | 1.34 | 0.88 |
| Gly | 3 | . | . | . | . | T | T | . | 0.07 | −0.17 | * | * | . | 1.91 | 1.06 |
| Arg | 4 | . | . | B | . | . | T | . | 0.57 | 0.09 | * | * | . | 0.98 | 0.89 |
| Ala | 5 | . | . | B | . | . | . | . | 0.64 | −0.53 | * | * | F | 2.20 | 1.12 |
| Pro | 6 | . | . | B | B | . | . | . | 0.39 | −0.47 | * | * | F | 1.48 | 1.63 |
| Leu | 7 | . | . | B | B | . | . | . | 0.39 | −0.26 | * | * | . | 0.96 | 0.62 |
| Arg | 8 | . | . | B | B | . | . | . | 0.39 | 0.17 | * | * | F | 0.29 | 0.95 |
| Thr | 9 | . | . | B | B | . | . | . | −0.31 | 0.10 | * | * | F | 0.07 | 0.61 |
| Val | 10 | . | . | B | . | . | T | . | −0.53 | 0.17 | * | * | F | 0.25 | 0.74 |
| Pro | 11 | . | . | B | . | . | T | . | −0.67 | 0.17 | * | . | F | 0.25 | 0.31 |
| Gly | 12 | . | . | B | . | . | T | . | −0.44 | 0.60 | * | . | F | −0.05 | 0.21 |
| Ala | 13 | . | . | B | . | . | T | . | −0.84 | 0.61 | * | . | . | −0.20 | 0.29 |
| Leu | 14 | . | A | B | B | . | . | . | −1.34 | 0.89 | . | . | . | −0.60 | 0.20 |
| Gly | 15 | . | A | B | B | . | . | . | −1.30 | 1.14 | . | . | . | −0.60 | 0.17 |
| Ala | 16 | . | A | B | B | . | . | . | −1.43 | 1.40 | . | . | . | −0.60 | 0.14 |
| Trp | 17 | . | A | B | B | . | . | . | −1.43 | 1.33 | . | . | . | −0.60 | 0.16 |
| Leu | 18 | . | A | B | B | . | . | . | −1.66 | 1.07 | . | . | . | −0.60 | 0.16 |
| Leu | 19 | . | A | B | B | . | . | . | −1.13 | 1.33 | . | . | . | −0.60 | 0.13 |
| Gly | 20 | . | A | . | B | T | . | . | −1.38 | 1.74 | . | . | . | −0.20 | 0.13 |
| Gly | 21 | . | . | . | B | . | . | C | −1.08 | 1.33 | . | . | . | −0.40 | 0.16 |
| Leu | 22 | . | . | . | B | T | . | . | −1.10 | 1.56 | . | . | . | −0.20 | 0.21 |
| Trp | 23 | . | . | . | B | T | . | . | −1.10 | 1.36 | . | . | . | −0.20 | 0.30 |
| Ala | 24 | . | . | B | B | . | . | . | −0.96 | 1.61 | . | . | . | −0.60 | 0.25 |
| Trp | 25 | . | . | B | B | . | . | . | −0.96 | 1.76 | . | . | . | −0.60 | 0.16 |
| Thr | 26 | . | . | B | B | . | . | . | −1.42 | 1.50 | . | . | . | −0.60 | 0.15 |
| Leu | 27 | . | . | B | B | . | . | . | −1.28 | 1.27 | . | . | . | −0.60 | 0.13 |
| Cys | 28 | . | . | . | B | T | . | . | −1.29 | 1.34 | . | . | . | −0.20 | 0.06 |
| Gly | 29 | . | . | . | B | T | . | . | −1.51 | 0.81 | . | . | . | −0.20 | 0.06 |
| Leu | 30 | . | . | . | B | T | . | . | −1.57 | 1.01 | . | . | . | −0.20 | 0.06 |
| Cys | 31 | . | . | B | . | . | T | . | −1.84 | 0.76 | . | . | . | −0.20 | 0.11 |
| Ser | 32 | . | . | B | . | . | T | . | −1.89 | 0.69 | . | . | . | −0.20 | 0.11 |
| Leu | 33 | . | . | B | . | . | T | . | −1.57 | 0.90 | . | . | . | −0.20 | 0.10 |
| Gly | 34 | . | . | B | . | . | T | . | −1.81 | 0.64 | . | . | . | −0.20 | 0.19 |
| Ala | 35 | . | . | B | B | . | . | . | −1.21 | 0.57 | . | . | . | −0.60 | 0.14 |
| Val | 36 | . | . | B | B | . | . | . | −0.43 | 0.61 | . | . | . | −0.60 | 0.26 |
| Gly | 37 | . | . | B | B | . | . | . | −0.34 | −0.07 | . | . | . | 0.58 | 0.52 |
| Ala | 38 | . | . | B | . | . | . | . | −0.20 | −0.07 | . | . | F | 1.21 | 0.80 |
| Pro | 39 | . | . | B | . | . | . | . | 0.14 | −0.00 | * | . | F | 1.49 | 0.58 |
| Arg | 40 | . | . | . | . | . | T | C | 0.14 | −0.24 | * | . | F | 2.32 | 1.01 |
| Pro | 41 | . | . | . | . | T | T | . | 0.79 | −0.17 | . | . | F | 2.80 | 1.01 |
| Cys | 42 | . | . | . | . | T | T | . | 1.13 | −0.24 | * | . | F | 2.52 | 1.01 |
| Gln | 43 | . | . | B | . | . | T | . | 1.72 | −0.27 | * | . | F | 1.69 | 0.89 |
| Ala | 44 | . | . | B | . | . | . | . | 1.64 | 0.13 | * | * | F | 0.61 | 1.00 |
| Pro | 45 | . | . | . | . | . | . | C | 1.53 | 0.61 | * | * | F | 0.58 | 1.96 |
| Gln | 46 | . | . | . | . | . | T | . | 1.40 | 0.04 | * | * | F | 1.00 | 1.96 |
| Gln | 47 | . | . | . | . | . | T | . | 2.18 | 0.07 | . | * | F | 1.20 | 1.92 |
| Trp | 48 | . | . | . | . | . | T | . | 2.18 | −0.43 | . | * | F | 2.00 | 2.43 |
| Glu | 49 | . | . | . | . | . | . | C | 1.91 | −0.46 | . | * | F | 2.00 | 2.43 |
| Gly | 50 | . | . | . | B | T | . | . | 1.52 | −0.21 | . | * | F | 1.80 | 1.04 |
| Arg | 51 | . | . | . | B | T | . | . | 1.28 | −0.00 | . | * | F | 1.45 | 0.98 |
| Gln | 52 | . | . | B | B | . | . | . | 1.28 | −0.16 | . | * | . | 0.70 | 0.89 |
| Val | 53 | . | . | B | B | . | . | . | 1.57 | 0.24 | . | * | . | 0.05 | 1.55 |
| Met | 54 | . | . | B | B | . | . | . | 1.27 | 0.21 | . | . | . | −0.15 | 1.37 |
| Tyr | 55 | . | . | B | B | . | . | . | 1.31 | 0.60 | * | . | . | −0.45 | 1.06 |
| Gln | 56 | . | . | B | B | . | . | . | 0.86 | 0.59 | * | . | F | 0.04 | 1.91 |
| Gln | 57 | . | . | B | B | . | . | . | 0.97 | 0.37 | . | . | F | 0.68 | 1.91 |
| Ser | 58 | . | . | . | . | . | T | C | 1.82 | −0.24 | . | . | F | 2.22 | 2.39 |
| Ser | 59 | . | . | . | . | . | T | C | 2.12 | −0.60 | * | . | F | 2.86 | 2.22 |
| Gly | 60 | . | . | . | . | T | T | . | 2.48 | −0.61 | * | . | F | 3.40 | 1.72 |
| Arg | 61 | . | . | . | . | T | T | . | 1.89 | −1.01 | * | . | F | 3.06 | 2.51 |
| Asn | 62 | . | . | . | . | . | T | C | 1.08 | −0.90 | * | . | F | 2.52 | 1.89 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 63 | . | . | B | . | . | T | . | 0.57 | −0.60 | * | . | F | 1.98 | 1.58 |
| Arg | 64 | . | . | B | . | . | T | . | 0.57 | −0.34 | * | . | F | 1.19 | 0.66 |
| Ala | 65 | . | . | B | . | . | T | . | 0.67 | 0.04 | * | * | . | 0.10 | 0.55 |
| Leu | 66 | . | . | B | . | . | . | . | 0.56 | 0.40 | * | * | . | −0.10 | 0.65 |
| Leu | 67 | . | . | B | . | . | . | . | 0.21 | 0.01 | . | * | . | −0.10 | 0.55 |
| Ser | 68 | . | . | B | . | . | T | . | −0.30 | 0.44 | . | * | . | −0.20 | 0.54 |
| Tyr | 69 | . | . | B | . | . | T | . | −0.41 | 0.63 | . | * | . | −0.20 | 0.54 |
| Asp | 70 | . | . | . | . | . | T | T | . | 0.18 | 0.34 | . | . | F | 0.80 | 1.06 |
| Gly | 71 | . | . | . | . | . | T | T | . | 1.10 | 0.06 | . | * | F | 0.80 | 1.36 |
| Leu | 72 | . | . | . | . | . | . | . | C | 1.06 | −0.33 | * | * | F | 1.00 | 1.70 |
| Asn | 73 | . | . | B | B | . | . | . | . | 1.47 | −0.44 | * | * | F | 0.45 | 0.76 |
| Gln | 74 | . | . | B | B | . | . | . | . | 0.86 | −0.44 | * | * | F | 0.60 | 1.50 |
| Arg | 75 | . | . | B | B | . | . | . | F | 0.04 | −0.23 | * | * | F | 0.60 | 1.35 |
| Val | 76 | . | A | B | B | . | . | . | . | 0.39 | −0.23 | * | * | . | 0.30 | 0.69 |
| Arg | 77 | . | A | B | B | . | . | . | . | 1.20 | −0.63 | * | * | . | 0.60 | 0.67 |
| Val | 78 | . | A | B | B | . | . | . | . | 1.31 | −1.03 | . | * | . | 0.60 | 0.59 |
| Leu | 79 | . | A | B | B | . | . | . | . | 1.36 | −1.03 | . | * | . | 0.75 | 1.56 |
| Asp | 80 | . | A | B | B | . | . | . | . | 0.66 | −1.67 | . | * | F | 0.90 | 1.59 |
| Glu | 81 | . | A | B | . | T | . | . | . | 0.70 | −1.17 | * | . | F | 1.30 | 2.16 |
| Arg | 82 | . | A | . | . | T | . | . | . | −0.30 | −1.13 | * | . | F | 1.30 | 2.16 |
| Lys | 83 | . | A | . | . | T | . | . | . | 0.34 | −1.13 | . | . | F | 1.15 | 0.91 |
| Ala | 84 | . | A | . | . | T | . | . | . | 0.49 | −0.70 | . | * | . | 1.00 | 0.81 |
| Leu | 85 | . | A | B | . | . | . | . | . | 0.53 | −0.13 | * | . | . | 0.30 | 0.22 |
| Ile | 86 | . | . | B | . | . | T | . | . | 0.64 | −0.13 | * | . | . | 0.70 | 0.22 |
| Pro | 87 | . | . | B | . | . | T | . | . | −0.28 | −0.13 | * | . | . | 0.70 | 0.43 |
| Cys | 88 | . | . | B | . | . | T | . | . | −1.02 | 0.06 | * | . | . | 0.10 | 0.43 |
| Lys | 89 | . | . | B | . | . | T | . | . | −0.43 | 0.16 | * | . | . | 0.10 | 0.53 |
| Arg | 90 | . | . | B | . | . | . | . | . | 0.13 | −0.53 | * | . | . | 0.80 | 0.60 |
| Leu | 91 | . | . | B | B | . | . | . | . | 0.13 | −0.20 | * | . | . | 0.45 | 1.74 |
| Phe | 92 | . | . | B | B | . | . | . | . | −0.47 | −0.09 | * | . | . | 0.30 | 0.61 |
| Glu | 93 | . | . | B | B | . | . | . | . | −0.61 | 0.60 | * | . | . | −0.60 | 0.26 |
| Tyr | 94 | . | . | B | B | . | . | . | . | −0.90 | 1.29 | * | . | . | −0.60 | 0.26 |
| Ile | 95 | . | . | B | B | . | . | . | . | −0.97 | 1.36 | * | . | . | −0.60 | 0.46 |
| Leu | 96 | . | . | B | B | . | . | . | . | −0.16 | 0.57 | . | . | . | −0.60 | 0.54 |
| Leu | 97 | . | . | B | B | . | . | . | . | 0.20 | 0.57 | . | . | . | −0.60 | 0.57 |
| Tyr | 98 | . | . | . | . | T | T | . | . | −0.66 | 0.24 | . | . | . | 0.50 | 0.81 |
| Lys | 99 | . | . | . | . | T | T | . | . | −1.01 | 0.20 | . | . | . | 0.50 | 0.73 |
| Asp | 100 | . | . | . | . | T | T | . | . | −0.82 | 0.13 | . | . | . | 0.50 | 0.87 |
| Gly | 101 | . | . | B | . | . | T | . | . | −0.01 | 0.23 | . | * | . | 0.10 | 0.48 |
| Val | 102 | . | . | B | B | . | . | . | . | −0.09 | −0.13 | . | * | . | 0.30 | 0.42 |
| Met | 103 | . | . | B | B | . | . | . | . | 0.16 | 0.56 | . | * | . | −0.60 | 0.18 |
| Phe | 104 | . | . | B | B | . | . | . | . | 0.11 | 0.56 | . | * | . | −0.60 | 0.30 |
| Gln | 105 | . | . | B | B | . | . | . | . | −0.48 | 0.53 | * | . | . | −0.30 | 0.69 |
| Ile | 106 | . | . | B | B | . | . | . | . | −0.44 | 0.39 | * | * | . | 0.30 | 0.70 |
| Asp | 107 | . | . | B | B | . | . | . | . | 0.46 | 0.26 | * | * | F | 0.90 | 1.17 |
| Gln | 108 | . | . | . | . | T | . | . | . | 1.06 | −0.53 | * | * | F | 2.70 | 1.36 |
| Ala | 109 | . | . | . | . | T | . | . | . | 1.09 | −0.53 | * | * | F | 3.00 | 3.35 |
| Thr | 110 | . | . | . | . | T | . | . | . | 0.79 | −0.64 | * | . | F | 2.70 | 1.07 |
| Lys | 111 | . | . | . | . | T | . | . | . | 1.72 | −0.26 | * | . | F | 1.95 | 0.83 |
| Gln | 112 | . | . | . | . | T | . | . | . | 1.12 | −0.66 | * | . | F | 2.10 | 1.65 |
| Cys | 113 | . | . | . | . | T | . | . | . | 0.81 | −0.54 | * | * | F | 1.80 | 1.13 |
| Ser | 114 | . | . | B | . | . | . | . | . | 0.59 | −0.54 | * | * | F | 0.95 | 0.81 |
| Lys | 115 | . | . | B | . | . | . | . | . | 0.59 | 0.14 | − | . | F | 0.05 | 0.39 |
| Met | 116 | . | . | B | . | . | . | . | . | 0.54 | 0.23 | . | . | . | 0.05 | 1.04 |
| Thr | 117 | . | . | B | . | . | . | . | . | 0.33 | 0.06 | . | . | . | 0.05 | 1.35 |
| Leu | 118 | . | . | B | . | . | . | . | . | 0.71 | 0.10 | . | * | F | 0.20 | 1.04 |
| Thr | 119 | . | . | B | . | . | . | . | . | 1.01 | 1.01 | . | * | F | −0.10 | 1.11 |
| Gln | 120 | . | . | B | . | . | . | . | . | 0.76 | 0.40 | * | * | F | 0.20 | 1.28 |
| Pro | 121 | . | . | . | . | . | T | . | . | 0.54 | 0.34 | * | . | F | 0.60 | 2.41 |
| Trp | 122 | . | . | . | . | . | T | . | . | 0.86 | 0.34 | * | . | F | 0.60 | 1.37 |
| Asp | 123 | . | . | . | . | . | T | C | . | 0.78 | −0.14 | * | . | F | 1.20 | 1.33 |
| Pro | 124 | . | . | B | . | . | T | . | . | 0.88 | 0.14 | . | . | F | 0.25 | 0.60 |
| Leu | 125 | . | . | . | . | T | T | . | . | 0.88 | 0.14 | . | . | F | 0.93 | 0.88 |
| Asp | 126 | . | . | B | . | . | T | . | . | 1.09 | −0.37 | . | . | F | 1.41 | 0.92 |
| Ile | 127 | . | . | . | . | . | . | C | . | 1.08 | 0.03 | . | . | F | 1.09 | 0.95 |
| Pro | 128 | . | . | . | . | . | T | C | . | 0.77 | −0.01 | . | . | F | 2.32 | 1.55 |
| Gln | 129 | . | . | . | . | . | T | . | . | 0.28 | −0.21 | . | * | F | 2.80 | 1.34 |
| Asn | 130 | . | . | . | . | . | T | C | . | 1.09 | 0.57 | . | * | F | 1.42 | 1.65 |
| Ser | 131 | . | . | . | . | . | T | C | . | 1.09 | −0.11 | . | * | F | 2.04 | 1.85 |
| Thr | 132 | . | . | B | . | . | . | . | . | 1.98 | −0.54 | . | . | F | 1.66 | 1.79 |
| Phe | 133 | . | . | B | . | . | . | . | . | 1.94 | −0.54 | . | . | F | 1.60 | 1.92 |
| Glu | 134 | . | . | B | . | . | . | . | . | 1.64 | −0.19 | . | * | F | 1.24 | 2.25 |
| Asp | 135 | . | . | B | . | . | T | . | . | 0.76 | −0.19 | . | * | F | 1.66 | 2.09 |
| Gln | 136 | . | . | B | . | . | T | . | . | 0.71 | 0.01 | . | * | . | 1.13 | 1.69 |
| Tyr | 137 | . | . | . | . | T | T | . | . | 0.68 | −0.34 | . | * | . | 2.20 | 0.97 |
| Ser | 138 | . | . | . | . | T | T | . | . | 1.17 | 0.09 | . | * | . | 1.38 | 0.57 |
| Ile | 139 | . | . | . | . | T | . | . | . | 1.17 | 0.51 | . | . | F | 0.97 | 0.51 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 140 | . | . | . | . | . | . | C | 1.17 | 0.51 | . | . | F | 0.71 | 0.56 |
| Gly | 141 | . | . | . | . | . | . | C | 1.17 | −0.24 | . | * | F | 1.55 | 0.73 |
| Pro | 142 | . | . | . | . | . | . | C | 0.52 | −0.23 | . | * | F | 1.64 | 1.80 |
| Gln | 143 | . | . | . | B | . | . | C | 0.51 | −0.23 | . | * | F | 1.60 | 1.28 |
| Glu | 144 | . | . | B | B | . | . | . | 0.54 | −0.17 | . | * | F | 1.24 | 1.86 |
| Gln | 145 | . | . | B | B | . | . | . | 0.89 | 0.04 | . | * | F | 0.33 | 0.89 |
| Ile | 146 | . | . | B | B | . | . | . | 1.23 | 0.01 | . | * | F | 0.17 | 0.89 |
| Thr | 147 | . | . | B | B | . | . | . | 1.16 | −0.39 | . | * | . | 0.46 | 0.89 |
| Val | 148 | . | . | B | B | . | . | . | 0.86 | 0.53 | . | * | . | −0.60 | 0.54 |
| Gln | 149 | . | . | B | B | . | . | . | 0.86 | 0.51 | . | * | . | −0.11 | 1.04 |
| Glu | 150 | . | . | B | B | . | . | . | 0.97 | −0.17 | . | * | F | 1.28 | 1.20 |
| Trp | 151 | . | . | . | . | T | T | . | 1.90 | −0.66 | . | . | F | 2.72 | 3.17 |
| Ser | 152 | . | . | . | . | T | T | C | 1.91 | −1.30 | . | . | F | 2.86 | 3.66 |
| Asp | 153 | . | . | . | . | T | T | . | 2.18 | −1.31 | * | * | F | 3.40 | 2.83 |
| Arg | 154 | . | . | . | . | T | T | . | 2.29 | −0.81 | . | * | F | 3.06 | 2.72 |
| Lys | 155 | . | . | . | . | T | . | . | 1.99 | −1.73 | * | * | F | 2.72 | 3.98 |
| Ser | 156 | . | . | . | . | . | . | C | 2.03 | −1.73 | * | * | F | 2.38 | 3.19 |
| Ala | 157 | . | . | . | . | . | T | C | 2.33 | −0.97 | * | . | F | 2.44 | 2.55 |
| Arg | 158 | . | . | . | . | . | T | C | 2.02 | −0.97 | * | * | F | 2.30 | 2.21 |
| Ser | 159 | . | . | B | . | . | T | . | 1.62 | −0.49 | * | * | F | 2.00 | 2.38 |
| Tyr | 160 | . | . | B | . | . | T | . | 0.69 | 0.04 | * | * | F | 1.20 | 2.48 |
| Glu | 161 | . | . | B | B | . | . | . | 0.64 | 0.23 | * | * | F | 0.45 | 0.89 |
| Thr | 162 | . | . | B | B | . | . | . | 0.34 | 0.66 | * | . | . | −0.20 | 0.65 |
| Trp | 163 | . | . | B | B | . | . | . | −0.01 | 0.96 | * | . | . | −0.40 | 0.29 |
| Ile | 164 | . | . | B | B | . | . | . | −0.02 | 0.96 | . | . | . | −0.60 | 0.27 |
| Gly | 165 | . | . | B | B | . | . | . | −0.63 | 1.44 | . | . | . | −0.60 | 0.27 |
| Ile | 166 | . | . | B | B | . | . | . | −0.59 | 1.60 | . | . | . | −0.60 | 0.19 |
| Tyr | 167 | . | . | B | B | . | . | . | −0.28 | 0.69 | . | . | . | −0.60 | 0.53 |
| Thr | 168 | . | . | B | B | . | . | . | −0.66 | −0.00 | . | . | . | 0.30 | 0.90 |
| Val | 169 | . | . | . | B | T | . | . | −0.01 | 0.14 | . | . | . | 0.24 | 0.69 |
| Lys | 170 | . | . | . | . | T | T | . | 0.12 | 0.21 | * | . | F | 0.93 | 0.69 |
| Asp | 171 | . | . | . | . | T | T | . | 0.16 | −0.11 | . | * | . | 1.52 | 0.74 |
| Cys | 172 | . | . | B | . | . | T | . | 0.40 | 0.04 | * | . | . | 0.66 | 0.74 |
| Tyr | 173 | . | . | B | . | . | T | . | 0.71 | −0.20 | * | . | . | 1.40 | 0.64 |
| Pro | 174 | . | . | B | . | . | . | . | 1.26 | −0.20 | * | * | . | 1.06 | 0.66 |
| Val | 175 | . | . | B | B | . | . | . | 0.51 | 0.29 | * | . | . | 0.27 | 1.78 |
| Gln | 176 | . | . | B | B | . | . | . | 0.20 | 0.50 | . | * | F | −0.17 | 0.99 |
| Glu | 177 | . | . | B | B | . | . | . | −0.02 | 0.23 | . | * | F | −0.01 | 0.92 |
| Thr | 178 | . | . | B | B | . | . | . | 0.22 | 0.49 | . | * | F | −0.45 | 0.87 |
| Phe | 179 | . | . | B | B | . | . | . | 0.19 | 0.24 | . | * | . | −0.30 | 0.81 |
| Thr | 180 | . | . | B | B | . | . | . | 0.74 | 0.60 | . | * | . | −0.60 | 0.73 |
| Ile | 181 | . | . | B | B | . | . | . | −0.11 | 0.99 | . | * | . | −0.60 | 0.68 |
| Asn | 182 | . | . | B | B | . | . | . | −1.00 | 1.14 | . | * | . | −0.60 | 0.58 |
| Tyr | 183 | . | . | B | B | . | . | . | −1.50 | 1.04 | . | * | . | −0.60 | 0.28 |
| Ser | 184 | . | . | B | B | . | . | . | −1.10 | 1.24 | . | * | . | −0.60 | 0.33 |
| Val | 185 | . | . | B | B | . | . | . | −1.10 | 0.94 | * | * | . | −0.60 | 0.28 |
| Ile | 186 | . | . | B | B | . | . | . | −0.10 | 1.03 | * | * | . | −0.60 | 0.25 |
| Leu | 187 | . | . | B | B | . | . | . | −0.80 | 0.27 | * | * | . | −0.30 | 0.37 |
| Ser | 188 | . | . | B | B | . | . | . | −1.26 | 0.67 | * | * | . | −0.60 | 0.43 |
| Thr | 189 | . | . | B | B | . | . | . | −0.96 | 0.81 | * | * | F | −0.45 | 0.54 |
| Arg | 190 | . | . | B | B | . | . | . | −0.99 | 0.13 | . | * | . | −0.15 | 1.09 |
| Phe | 191 | . | . | B | B | . | . | . | −0.10 | 0.13 | . | * | . | −0.30 | 0.57 |
| Phe | 192 | . | . | B | B | . | . | . | −0.10 | 0.14 | . | * | . | −0.30 | 0.68 |
| Asp | 193 | . | . | B | B | . | . | . | −0.14 | 0.34 | * | * | . | −0.30 | 0.29 |
| Ile | 194 | . | . | B | B | . | . | . | −0.72 | 0.77 | * | * | . | −0.60 | 0.33 |
| Gln | 195 | . | . | B | B | . | . | . | −0.79 | 0.67 | * | * | . | −0.60 | 0.27 |
| Leu | 196 | . | . | B | B | . | . | . | −0.09 | −0.11 | * | * | . | 0.51 | 0.32 |
| Gly | 197 | . | . | . | . | T | . | . | 0.40 | −0.11 | * | * | . | 1.32 | 0.76 |
| Ile | 198 | . | . | . | . | T | . | . | 0.10 | −0.37 | * | * | . | 1.53 | 0.68 |
| Lys | 199 | . | . | . | . | . | . | C | 0.13 | −0.39 | * | * | F | 1.84 | 1.10 |
| Asp | 200 | . | . | . | . | . | T | C | −0.57 | −0.43 | . | * | F | 2.10 | 0.83 |
| Pro | 201 | . | . | B | . | . | T | . | −0.07 | −0.07 | . | . | F | 1.84 | 1.02 |
| Ser | 202 | . | . | B | . | . | T | . | 0.07 | −0.27 | . | . | F | 1.48 | 0.74 |
| Val | 203 | . | . | B | . | . | T | . | 0.74 | 0.16 | . | . | . | 0.52 | 0.68 |
| Phe | 204 | . | . | B | . | . | . | . | 0.40 | 0.59 | . | . | . | −0.19 | 0.68 |
| Thr | 205 | . | . | . | . | . | . | C | 0.09 | 0.54 | . | . | F | −0.05 | 0.68 |
| Pro | 206 | . | . | . | . | . | T | C | −0.37 | 0.64 | . | . | F | 0.30 | 1.32 |
| Pro | 207 | . | . | . | . | T | T | . | −0.07 | 0.57 | . | . | F | 0.35 | 0.82 |
| Ser | 208 | . | . | . | . | T | T | . | 0.19 | 0.19 | . | . | F | 0.65 | 0.98 |
| Thr | 209 | . | . | . | . | T | T | . | 0.30 | 0.31 | . | . | F | 0.65 | 0.63 |
| Cys | 210 | . | A | B | . | . | . | . | 0.61 | 0.39 | . | . | . | −0.30 | 0.41 |
| Gln | 211 | . | A | B | . | . | . | . | 0.01 | 0.36 | . | . | . | −0.30 | 0.53 |
| Met | 212 | . | A | B | . | . | . | . | 0.22 | 0.66 | . | . | . | −0.60 | 0.30 |
| Ala | 213 | . | A | B | . | . | . | . | 0.57 | 0.17 | . | . | . | −0.30 | 0.98 |
| Gln | 214 | A | A | . | . | . | . | . | 0.28 | −0.40 | . | . | . | 0.45 | 1.13 |
| Leu | 215 | A | A | . | . | . | . | . | 0.64 | −0.19 | . | . | . | 0.76 | 1.13 |
| Glu | 216 | . | A | B | . | . | . | . | 0.64 | −0.41 | * | . | . | 1.07 | 1.50 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 217 | . | A | B | . | . | . | . | 1.24 | −0.91 | * | . | F | 1.83 | 1.50 |
| Met | 218 | . | A | . | . | T | . | . | 1.17 | −1.31 | * | . | F | 2.54 | 3.05 |
| Ser | 219 | . | . | . | . | T | T | . | 0.87 | −1.43 | * | . | F | 3.10 | 0.94 |
| Glu | 220 | . | . | . | . | T | T | . | 1.39 | −1.04 | * | . | F | 2.79 | 0.63 |
| Asp | 221 | . | . | . | . | T | T | . | 1.00 | −0.13 | . | * | F | 2.18 | 0.67 |
| Cys | 222 | . | . | . | . | T | T | . | 0.57 | −0.31 | . | * | . | 1.72 | 0.64 |
| Ser | 223 | . | . | . | . | T | . | . | 0.78 | −0.27 | . | . | . | 1.21 | 0.47 |
| Trp | 224 | . | . | . | . | T | . | . | 0.69 | 0.16 | . | . | . | 0.30 | 0.36 |

Among highly preferred fragments in this regard are those that comprise regions of Human Ependymin that combine several structural features, such as several of the features set out above.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209464. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the Ependymin cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a Ependymin polypeptide may include, but are not limited to those encoding the amino acid sequence of the mature polypeptide, by itself; and the coding sequence for the mature polypeptide and additional sequences, such as those encoding the about 37 amino acid leader or secretory sequence, such as a pre-, or pro- or prepro- protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the Ependymin fused to Fc at the N- or C-terminus.

Variant and Mutant Polynucleotides

The present invention further relates to variants of the nucleic acid molecules of the present invention, which encode portions, analogs or derivatives of the Ependymin protein. Variants may occur naturally, such as a natural allelic variant. By an "allelic variant" is intended one of several alternate forms of a gene occupying a given locus on a chromosome of an organism (Genes II, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Ependymin protein or portions thereof. Also especially preferred in this regard are conservative substitutions.

Most highly preferred are nucleic acid molecules encoding the mature protein having the amino acid sequence shown in SEQ ID NO:2 or the mature Ependymin amino acid sequence encoded by the deposited cDNA clone.

Thus, one aspect of the invention provides an isolated nucleic acid molecule comprising a polynucleotide having a nucleotide sequence selected from the group consisting of: (a) a nucleotide sequence encoding the Ependymin polypeptide having the complete amino acid sequence in SEQ ID NO:2 (i.e., positions −37 to 187 of SEQ ID NO:2); (b) a nucleotide sequence encoding the Ependymin polypeptide having the complete amino acid sequence in SEQ ID NO:2 excepting the N-terminal methionine (i.e., positions −36 to 187 of SEQ ID NO:2); (c) a nucleotide sequence encoding the predicted mature Ependymin polypeptide having the amino acid sequence at positions 1 to 187 in SEQ ID NO:2; (d) a nucleotide sequence encoding the Ependymin polypeptide having the complete amino acid sequence encoded by the cDNA clone contained in ATCC Deposit No. 209464; (e) a nucleotide sequence encoding the Ependymin polypeptide having the complete amino acid sequence excepting the N-terminal methionine encoded by the cDNA clone contained in ATCC Deposit No. 209464; (f) a nucleotide sequence encoding the mature Ependymin polypeptide having the amino acid sequence encoded by the cDNA clone contained in ATCC Deposit No. 209464; and (g) a nucleotide sequence complementary to any of the nucleotide sequences in (a), (b), (c), (d), (e) or (f), above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a Ependymin polypeptide having an amino acid sequence in (a), (b), (c), (d), (e) or (f), above. A further nucleic acid embodiment of the invention relates to an isolated nucleic acid molecule comprising a polynucleotide which encodes the amino acid sequence of a Ependymin polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a polynucleotide which encodes the amino acid sequence of a Ependymin polypeptide to have an amino acid sequence which contains not more than 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of Ependymin polypeptides or peptides by recombinant techniques.

By a polynucleotide having a nucleotide sequence at least, for example, 95% "identical" to a reference nucleotide sequence encoding a Ependymin polypeptide is intended that the nucleotide sequence of the polynucleotide is identical to the reference sequence except that the polynucleotide sequence may include up to five point mutations per each 100 nucleotides of the reference nucleotide sequence encoding the Ependymin polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A, 1B, and 1C, or to the nucleotides sequence of the deposited cDNA clone HDPIE88 can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=, 1 Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA, irrespective of whether they encode a polypeptide having Ependymin activity. This is because even where a particular nucleic acid molecule does not encode a polypeptide having Ependymin activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Ependymin activity include, inter alia, (1) isolating the Ependymin gene or allelic variants thereof in a cDNA library; (2) in situ hybridization (e.g., "FISH") to metaphase chromosomal spreads to provide precise chromosomal location of the Ependymin gene, as described by Verma and colleagues (*Human Chromosomes: A Manual of Basic Techniques*, Pergamon Press, New York (1988)); and Northern Blot analysis for detecting Ependymin mRNA expression in specific tissues.

Preferred, however, are nucleic acid molecules having sequences at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA which do, in fact, encode a polypeptide having Ependymin protein activity. By "a polypeptide having Ependymin activity" is intended polypeptides exhibiting activity similar, but not necessarily identical, to an activity of the mature Ependymin protein of the invention, as measured in a particular biological assay. For example, the Ependymin protein of the present invention binds $Ca^{2+}$ to a high degree. Maruyama and colleagues (*J. Biochem.* 95:511–519 (1984)), Ganss and Hoffmuan (*Eur. J. Biochem.* 217:275–280 (1993)), and Schmidt and Makiola (*Neuro. Chem.* (*Life Sci. Adv.*) 10:161–171 (1991)) each demonstrate a convenient laboratory method to determine and roughly quantitate the amount of radiolabeled $Ca^{2+}$ which a given polypeptide, such as Ependymin of the present invention, can bind. Briefly, 5–10 µg protein is used for each analysis. The protein samples are separated by conventional SDS/PAGE using a 13% polyacrylamide gel according to methods which are well-known to one of ordinary skill in the art. Following SDS/PAGE, the proteins are transferred to a nitrocellulose filter also according to methods which are well-known to one of ordinary skill in the art (for example, such a method is provided by Towbin, H., et al., *Proc. Natl. Acad. Sci. USA* 76:4350–4354 (1979)). After the protein is transferred to the nitrocellulose filter, the blot is hybridized with 200 ml $^{45}CaCl_2$ (300 µCi) in the presence of 5 mM $MgCl_2$. To reduce non-specific binding of $Ca^{2+}$, the transfer buffer is washed out by three changes (20 minutes each) of 10 mM imidazole/HCl buffer, pH 6.8, containing 5 mM $MgCl_2$ and 60 mM KCl. In such analyses, it is convenient to use a well-known, strong $Ca^{2+}$-binding protein, such as calmodulin (Pharmacia) and a well-known, protein which does not bind $Ca^{2+}$, such as bovine serum albumin (Sigma) as controls. To quantitate the amount of $Ca^{2+}$ bound to a specific protein, the region of the nitrocellulose filter which to which the protein is bound is cut out and placed in a standard scintillation vial. The vial is then filled with 4 ml scintillation cocktail (for example, Quickszint 361; Zinsser, Maidenhead, U.K.) and counted in a liquid scintillation counter (for example, the Wallac 1410, Pharmacia). Using such an analysis, one of ordinary skill in the art may easily ascertain useful qualitative and quantitative information regarding proteins such as Ependymin, or muteins thereof, of the present invention such as the amount of $Ca^{2+}$ that the protein will bind and the apparent molecular mass of the protein. $Ca^{2+}$-binding activity is a useful indicator of the potential for more complex biological activities.

Ependymin protein binds $Ca^{2+}$ in a dose-dependent manner in the above-described assay. Thus, "a polypeptide having Ependymin protein activity" includes polypeptides that also exhibit any of the same $Ca^{2+}$-binding activities in the above-described assays in a dose-dependent manner. Although the degree of dose-dependent activity need not be identical to that of the Ependymin protein, preferably, "a polypeptide having Ependymin protein activity" will exhibit substantially similar dose-dependence in a given activity as compared to the Ependymin protein (i.e., the candidate polypeptide will exhibit greater activity or not more than about 25-fold less and, preferably, not more than about tenfold less activity relative to the reference Ependymin protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A, 1B, and 1C (SEQ ID NO:1) will encode a polypeptide "having Ependymin protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ependymin protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of Ependymin polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and *Bowes melanoma* cells; and plant cells. Appropriate culture mediums and conditions for the above-described host cells are known in the art.

Vectors preferred for use in bacteria include pHE4-5 (ATCC Accession No. 209311; and variations thereof), pQE70, pQE60 and pQE-9 (QIAGEN, Inc., supra); pBS vectors, Phagescript vectors, Bluescript vectors, pNH8A, pNH16a, pNH18A, pNH46A (Stratagene); and ptrc99a, pKK223-3, pKK233-3, pDR540, pRIT5 (Pharmacia). Among preferred eukaryotic vectors are pWLNEO, pSV2CAT, pOG44, pXT1, and pSG (Stratagene); and pSVK3, pBPV, pMSG and pSVL (Pharmacia). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52–58 (1995); Johanson, K., et al., *J. Biol. Chem.* 270:9459–9471 (1995)).

The Ependymin protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated Ependymin polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of Ependymin polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. In the present case, since the protein of the invention is a member of the ependymin polypeptide family, deletions of N-terminal amino acids up to the cysteine at position 5 of SEQ ID NO:2 may retain some biological activity such as $Ca^{2+}$-binding or the ability to modulate regeneration. Polypeptides having further N-terminal deletions including the Cys-5 residue in SEQ ID NO:2 would not be expected to retain such biological activities because this residue is conserved in each of the ependymin-related polypeptides shown in FIGS. 3A and 3B and it is likely that a cysteine in such a position may be required for forming a disulfide bridge to provide structural stability which is needed for receptor binding and signal transduction.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the. Ependymin shown in SEQ ID NO:2, up to the cysteine residue at position number 5, and polynucleotides encoding such polypeptides. In particular, the present invention provides polypeptides comprising the amino acid sequence of residues $n^1$-187 of SEQ ID NO:2, where $n^1$ is an integer in the range of –37 to 4, and 5 is the position of the first residue from the N-terminus of the complete Ependymin polypeptide (shown in SEQ ID NO:2) believed to be required for the $Ca^{2+}$-binding or the regeneration modulatory activities of the Ependymin protein.

More in particular, the invention provides polynucleotides encoding polypeptides having the amino acid sequence of residues of –37-187, –36-187, –35-187, –34-187, –33-187, –32-187, –31-187, –30-187, –29-187, –28-187, –27-187, –26-187, –25-187, –24-187, –23-187, –22-187, –21-187, –20-187, –19-187, –18-187, –17-187, –16-187, –15-187, –14-187, –13-187, –12-187, –11-187, –10-187, –9-187, –7-187, –6-187, –5-187, –4-187, –3-187, –2-187, –1-187, 1-187, –2-187, 3-187, 4-187, and 5-187 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)). In the present case, since the protein of the invention is a member of the ependymin polypeptide family, deletions of C-terminal amino acids up to the cysteine at position 173 of SEQ ID NO:2 may retain some biological activity such as $Ca^{2+}$-binding or the ability to modulate regeneration. Polypeptides having further C-terminal deletions including the cysteine residue at position 173 of SEQ ID NO:2 would not be expected to retain such biological activities because this residue is conserved in each of the ependymin-related polypeptides shown in FIGS. 3A and 3B and it is likely that a cysteine in such a position may be required for forming a disulfide bridge to provide structural stability which is needed for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the Ependymin shown in SEQ ID NO:2, up to the cysteine residue at position 173 of SEQ ID NO:2, and polynucleotides encoding such polypeptides. In particular, the present invention provides polypeptides having the amino acid sequence of residues $-37$-$m^1$ of the amino acid sequence in SEQ ID NO:2, where ml is any integer in the range of 173 to 187, and residue 173 is the position of the first residue from the C-terminus of the complete Ependymin polypeptide (shown in SEQ ID NO:2) believed to be required for the $Ca^{2+}$-binding or the regeneration modulatory abilities of the Ependymin protein.

More in particular, the invention provides polynucleotides encoding polypeptides having the amino acid sequence of residues –37-173, –37-174, –37-175, –37-176, –37-177, –37-178, –37-179, –37-180, –37-181, –37-182, –37-183, –37-184, –37-185, –37-186, and –37-187 of SEQ ID NO:2. Polynucleotides encoding these polypeptides also are provided.

The invention also provides polypeptides having one or more amino acids deleted from both the amino and the carboxyl termini, which may be described generally as having residues $n^1m^1$ of SEQ ID NO:2, where $n^1$ and $m^1$ are integers as described above.

Also included are a nucleotide sequence encoding a polypeptide consisting of a portion of the complete Ependymin amino acid sequence encoded by the cDNA clone contained in ATCC Deposit No. 209464, where this portion excludes from 1 to about 42 amino acids from the amino terminus of the complete amino acid sequence encoded by the cDNA clone contained in ATCC Deposit No. 209464, or from 1 to about 15 amino acids from the carboxy terminus, or any combination of the above amino terminal and carboxy terminal deletions, of the complete amino acid sequence encoded by the cDNA clone contained in ATCC Deposit No. 209464. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened Human Ependymin mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a Human Ependymin mutein with a large number of deleted N-terminal amino acid residues may retain some biological or immungenic activities. In fact, peptides composed of as few as six Human Ependymin amino acid residues may often evoke an immune response.

Accordingly, the present invention further provides polypeptides having one or more residues deleted from the amino terminus of the Human Ependymin amino acid sequence shown in SEQ ID NO:2, up to the serine acid residue at position number 219 and polynucleotides encoding such polypeptides. In particular, the present invention provides polypeptides comprising the amino acid sequence of residues $n^2$-224 of FIGS. 1A, 1B, and 1C (SEQ ID NO:2), where $n^2$ is an integer in the range of 2 to 219, and 220 is the position of the first residue from the N-terminus of the complete Human Ependymin polypeptide believed to be required for at least immunogenic activity of the Human Ependymin protein.

More in particular, the invention provides polynucleotides encoding polypeptides comprising, or alternatively consisting of, the amino acid sequence of residues of P-2 to W-224; G-3 to W-224; R-4 to W-224; A-5 to W-224; P-6 to W-224; L to W-224; R-8 to W-224; T-9 to W-224; V-10 to W-224; P-11 to W-224; G-12 to W-224; A-13 to W-224; L-14 to W-224; G-15 to W-224; A-16 to W-224; W-17 to W-224; L-18 to W-224; L-19 to W-224; G-20 to W-224; G-21 to W-224; L-22 to W-224; W-23 to W-224; A-24 to W-224; W-25 to W-224; T-26 to W-224; L-27 to W-224; C-28 to W-224; G-29 to W-224; L-30 to W-224; C-31 to W-224; S-32 to W-224; L-33 to W-224; G-34 to W-224; A-35 to W-224; V-36 to W-224; G-37 to W-224; A-38 to W-224; P-39 to W-224; R-40 to W-224; P-41 to W-224; C-42 to W-224; Q-43 to W-224; A-44 to W-224; P-45 to W-224; Q-46 to W-224; Q-47 to W-224; W-48 to W-224; E-49 to W-224; G-50 to W-224; R-51 to W-224; Q-52 to W-224; V-53 to W-224; M-54 to W-224; Y-55 to W-224; Q-56 to W-224; Q-57 to W-224; S-58 to W-224; S-59 to W-224; G-60 to W-224; R-61 to W-224; N-62 to W-224; S-63 to W-224; R-64 to W-224; A-65 to W-224; L-66 to W-224; L-67 to W-224; S-68 to W-224; Y-69 to W-224; D-70 to W-224; G-71 to W-224; L-72 to W-224; N-73 to W-224; Q-74 to W-224; R-75 to W-224; V-76 to W-224; R-77 to W-224; V-78 to W-224; L-79 to W-224; D-80 to W-224; E-81 to W-224; R-82 to W-224; K-83 to W-224; A-84 to W-224; L-85 to W-224; I-86 to W-224; P-87 to W-224; C-88 to W-224; W-224; R-90 to W-224; L-91 to W-224; F-92 to W-224; E-93 to W-224; Y-94 to W-224; I-95 to W-224; L-96 to W-224; L-97 to W-224; Y-98 to W-224; K-99 to W-224; D-100 to W-224; G-101 to W-224; V-102 to W-224; M-103 to W-224; F-104 to W-224; Q-105 to W-224; I-106 to W-224; D-107 to W-224; Q-108 to W-224; A-109 to W-224; T-10 to W-224; K-111 to W-224; Q-112 to W-224; C-113 to W-224; S-114 to W-224; K-115 to W-224; M-116 to W-224; T-117 to W-224; L-118 to W-224; T-119 to W-224; Q-120 to W-224; P-121 to W-224; W-122 to W-224; D-123 to W-224; P-124 to W-224; L-125 to W-224; D-126 to W-224; I-127 to W-224; P-128 to W-224; Q-129 to W-224; N-130 to W-224; S-131 to W-224; T-132 to W-224; F-133 to W-224; E-134 to W-224; D-135 to W-224; Q-136 to W-224; Y-137 to W-224; S-138 to W-224; I-139 to W-224; G-140 to W-224; G-141 to W-224; P-142 to W-224; Q-143 to W-224; E-144 to W-224; Q-145 to W-224; I-146 to W-224; T-147 to W-224; V-148 to W-224; Q-149 to W-224; E-150 to W-224; W-151 to W-224; S-152 to W-224; D-153 to W-224; R-154 to W-224; K-155 to W-224; S-156 to W-224; A-157 to W-224; R-158 to W-224; S-159 to W-224; Y-160 to W-224; E-161 to W-224; T-162 to W-224; W-163 to W-224; I-164 to W-224; G-165 to W-224; I-166 to W-224; Y-167 to W-224; T-168 to W-224; V-169 to W-224; K-170 to W-224; D-171 to W-224; C-172 to W-224; Y-173 to W-224; P-174 to W-224; V-175 to W-224; Q-176 to W-224; E-177 to W-224; T-178 to W-224; F-179 to W-224; T-180 to W-224; I-181 to W-224; N-182 to W-224; Y-183 to W-224; S-184 to W-224; V-185 to W-224; I-186 to W-224; L-187 to W-224; S-188 to W-224; T-189 to W-224; R-190 to W-224; F-191 to W-224; F-192 to W-224; D-193 to W-224; I-194 to W-224; Q-195 to W-224; L-196 to W-224; G-197 to W-224; I-198 to W-224; K-199 to W-224; D-200 to W-224; P-201 to W-224; S-202 to W-224; V-203 to W-224; F-204 to W-224; T-205 to W-224; P-206 to W-224; P-207 to W-224; S-208 to W-224; T-209 to W-224; C-210 to W-224; Q-211 to W-224; M-212 to W-224; A-213 to W-224; Q-214 to W-224; L-215 to W-224; E-216 to W-224; K-217 to W-224; M-218 to W-224; and S-219 to W-224 of the Human Ependymin amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 224 from the N-terminus to the C-terminus, while the amino acid residues in SEQ ID NO:2 are numbered consecutively from −37 through 187 to reflect the position of the predicted signal peptide). Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened Human Ependymin mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a Human Ependymin mutein with a large number of deleted C-terminal amino acid residues may retain some biological or immungenic activities. In fact, peptides composed of as few as six Human Ependymin amino acid residues may often evoke an immune response.

Accordingly, the present invention further provides polypeptides having one or more residues deleted from the carboxy terminus of the amino acid sequence of the Human Ependymin shown in SEQ ID NO:2, up to the proline residue at position number 6, and polynucleotides encoding such polypeptides. In particular, the present invention provides polypeptides comprising the amino acid sequence of residues 1-$m^2$ of SEQ ID NO:2, where $m^2$ is an integer in the range of 6 to 224, and 6 is the position of the first residue from the C-terminus of the complete Human Ependymin polypeptide believed to be required for at least immunogenic activity of the Human Ependymin protein.

More in particular, the invention provides polynucleotides encoding polypeptides comprising, or alternatively consisting of, the amino acid sequence of residues M-1 to S-223; M-1 to C-222; M-1 to D-221; M-1 to E-220; M-1 to S-219; M-1 to M-218; M-1 to K-217; M-1 to E-216; M-1 to L-215; M-1 to Q-214; M-1 to A-213; M-212; M-1 to Q-211; M-1 to C-210; M-1 to T-209; M-1 to S-208; M-1 to P-207; M-1 to P-206; M-1 to T-205; M-1 to F-204; M-1 to V-203; M-1 to S-202; M-1 to P-201; D-200; M-1 to K-199; M-1 to 1-198; M-1 to G-197; M-1 to L-196; M-1 to Q-195; M-1 to I-194; M-1 to D-193; M-1 to F-192; M-1 to F-191; M-1 to R-190; M-1 to T-189; M-1 to S-188; M-1 to L-187; M-1 to I-186; M-1 to V-185; M-1 to S-184; M-1 to Y-183; M-1 N-182; M-1 to I-181; M-1 to T-180; M-1 to F-179; M-1 to T-178; M-1 to E-177; M-1 to Q-176; M-1 to V-175; M-1 to P-174; M-1 Y-173; M-1 to C-172; M-1 to D-171; M-1 to K-170; M-1 to V-169; M-1 to T-168; M-1 to Y-167; M-1 to I-166; M-1 to G-165; M-1 to I-164; M-1 to W-163; M-1 to T-162; M-1 to E-161; M-1 to Y-160; M-1 to S-159; R-158; M-1 to A-157; M-1 to S-156; M-1 to K-155; M-1 to R-154; M-1 to D-153; M-1 to S-152; M-1 to W-151; M-1 to E-150; M-1 to Q-149; M-1 to V-148; M-1 to T-147; M-1 to I-146; M-1 to Q-145; M-1 to E-144; M-1 to Q-143; M-1 to P-142; M-1 to G-141; M-1 to G-140; M-1 to I-139; M-1 to S-138; M-1 to Y-137; M-1 to Q-136; M-1 to D-135; M-1 to E-134; M-1 to F-133; M-1 to T-132; M-1 to S-131; M-1 to N-130; M-1 to Q-129; M-1 to P-128; M-1 to I-127; M-1 to D-126; M-1 to L-125; M-1 to P-124; M-1 to D-123; M-1 to W-122; M-1 to P-121; M-1 to Q-120; M-1 to T-119; M-1 to L-118; M-1 to T-117; M-1 to M-116; M-1 to K-115; M-1 to S-114; M-1 to C-113; M-1 to Q-112; M-1 to K-111; M-1 to T-110; M-1 to A-109; M-1 to Q-108; M-1 to D-107; M-1 to I-106; M-1 to Q-105; M-1 to F-104; M-1 to M-103; M-1 to V-102; M-1 to G-101; M-1 to D-100; M-1 to K-99; M-1 to Y-98; M-1 to L-97; M-1 to L-96; M-1 to I-95; M-1 to Y-94; M-1 to E-93; M-1 to F-92; M-1 to L-91; M-1 to R-90; M-1 to K-89; M-1 to C-88; M-1 to P-87; M-1 to 1 to L-85; M-1 to A-84; M-1 to K-83; M-1 to R-82; M-1 to E-81; M-1 to D-80; M-1 to M-1 to V-78; M-1 to R-77; M-1 to V-76; M-1 to R-75; M-1 to Q-74; M-1 to N-73; M-1 to L-72; M-1 to G-71; M-1 to D-70; M-1 to Y-69; M-1 to S-68; M-1 to L-67; M-1 to L66; M-1 to A-65; M-1 to R-64; M-1 to S-63; M-1 to N-62; M-1 to R-61; M-1 to G-60; M-1 to S-59; M-1 to S-58; M-1 to Q-57; M-1 to Q-56; M-1 to Y-55; M-1 to M-54; M-1to V-53; M-1to Q-52; M-1 to R-51; M-1 to G-50; M-1 to E-49; M-1 to W-48; M-1 to Q-47; M-1 to Q-46; M-1 to P-45; M-1 to A-44; M-1 to Q-43; M-1 to C-42; M-1 to P-41; M-1 to R-40; M-1 to P-39; M-1 to A-38; M-1 to G-37; M-1 to V-36; M-1 to A-35; M-1 to G-34; M-1 to L-33; M-1 to S-32; M-1 to C-31; M-1 to L-30; M-1 to G-29; M-1 to C-28; M-1 to L-27; M-1 to T-26; M-1 to W-25; M-1 to A-24; M-1 to W-23; M-1 to L-22; M-1 to G-21; M-1 to G-20; M-1 to L-19; M-1 to L-18; M-1 to W-17; M-1 to A-16; M-1 to G-15; M-1 L-14; M-1 to A-13; M-1 to G-12; M-1 to P-11; M-1 to V-10; M-1 to T-9; M-1 to R-8; M to L-7; M-1 to P-6 of the sequence of the Human Ependymin sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 224 from the N-terminus to the C-terminus, while the amino acid residues in SEQ ID NO:2 are numbered consecutively from −37 through 187 to reflect the position of the predicted signal peptide). Polynucleotides encoding these polypeptides also are provided.

The invention also provides polypeptides having one or more amino acids deleted from both the amino and the carboxyl termini of a Human Ependymin polypeptide, which may be described generally as having residues $n^2$-$m^2$ of FIGS. 1A, 1B, and 1C (SEQ ID NO:2), where $n^2$ and $m^2$ are integers as described above.

Other Mutants

In addition to terminal deletion forms of the protein discussed above, it also will be recognized by one of ordinary skill in the art that some amino acid sequences of the Ependymin polypeptide can be varied without significant effect of the structure or function of the protein. If such differences in sequence are contemplated, it should be remembered that there will be critical areas on the protein which determine activity.

Thus, the invention further includes variations of the Ependymin polypeptide which show substantial Ependymin polypeptide activity or which include regions of Ependymin protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306–1310 (1990)),. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side-chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the Ependymin of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the Ependymin protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377 (1993)).

Replacement of amino acids can also change the selectivity of the binding of a ligand to cell surface receptors (for example, Ostade, et al., *Nature* 361:266–268 (1993)) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith, et al., *J. Mol. Biol.* 224:899–904 (1992); de Vos, et al. *Science* 255:306–312 (1992)).

As described above, ependymin function relies, in part, on asparagine-linked glycosylation. Although the relative locations of the two potential N-linked glycosylation sites of Ependymin of the present invention are not conserved with respect to the other known ependymins, it is likely that disruption of the either or both of the Ependymin glycosylation sites will, at least, modulate Ependymin activity. As a result, mutation of the asparagine amino acid residues at positions 93 and 145 of SEQ ID NO:2 or the threonine or serine amino acid residues at positions 95 and 147, respectively, will, at least modulate the biological activity of Ependymin of the present invention.

In addition, as depicted in FIGS. 2 and 3, five cysteine amino acid residues are conserved between Ependymin of the present invention and five piscine ependymin homologs. Since cysteine amino acid residues often function in a structural capacity with respect to the tertiary structure of a polypeptide (or the quaternary structure of the same polypeptide in cases where polymerization is expected), it is expected that mutation of any or all of the four conserved cysteine amino acid residues will result in, at least, modulation of the biological activity of Ependymin of the present invention. As shown in FIGS. 3A and 3B, the conserved cysteine residues are located at positions 5, 51, 76, 135, and 173 of SEQ ID NO:2.

Similarly, several additional amino acids are highly conserved between Ependymin of the present invention and the five piscine ependymins presented in FIGS. 3A and 3B. These are Proline-8, Tyrosine-32, Aspartic Acid-33, Glycine-64, Isoleucine-69, Aspartic Acid-70, Lysine-78, Leucine-8 1, Proline-9 1, Glycine-103, Tryptophan-114, Threonine-131, Phenylalanine-167, Proline-170, and Glutamic Acid-179. It is expected that mutation of one, several, or all of these amino acid residues will modulate the biological activity of Ependymin of the present invention.

Mutations which may also modulate, and are less likely to completely eliminate, the biological activity of Ependymin of the present invention may also be made by changing one or more non-conserved amino acid residues throughout the Ependymin polypeptide. Also forming part of the present invention are isolated polynucleotides comprising nucleic acid sequences which encode the each of the above Ependymin mutants.

The polypeptides of the present invention are preferably provided in an isolated form, and preferably are substantially purified. A recombinantly produced version of the Ependymin polypeptide can be substantially purified by the one-step method described by Smith and Johnson (*Gene* 67:31–40 (1988)). Polypeptides of the invention also can be purified from natural or recombinant sources using anti-Ependymin antibodies of the invention in methods which are well known in the art of protein purification.

The invention further provides an isolated Ependymin polypeptide comprising an amino acid sequence selected from the group consisting of: (a) the amino acid sequence of the full-length Ependymin polypeptide having the complete amino acid sequence shown in SEQ ID NO:2 (i.e., positions −37 to 187 of SEQ ID NO:2); (b) the amino acid sequence of the full-length Ependymin polypeptide having the complete amino acid sequence shown in SEQ ID NO:2 excepting the N-terminal methionine (i.e., positions −36 to 187 of SEQ ID NO:2); (c) the amino acid sequence of the predicted mature Ependymin polypeptide having the amino acid sequence at positions 1 to 187 in SEQ ID NO:2; (d) the complete amino acid sequence encoded by the cDNA clone contained in the ATCC Deposit No. 209464; (e) the complete amino acid sequence excepting the N-terminal methionine encoded by the cDNA clone contained in the ATCC Deposit No. 209464; and (f) the complete amino acid sequence of the predicted mature Ependymin polypeptide encoded by the cDNA clone contained in the ATCC Deposit No. 209464. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f), above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

A further embodiment of the invention relates to a peptide or polypeptide which comprises the amino acid sequence of a Ependymin polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a peptide or polypeptide to have an amino acid sequence which comprises the amino acid sequence of a Ependymin polypeptide, which contains at least one, but not more than 10, 9, 8, 7, 6, 5, 4, 3, 2 or 1 conservative amino acid substitutions.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a Ependymin polypeptide is intended that the amino acid sequence of the polypeptide is identical to the reference sequence except that the polypeptide sequence may include up to five amino acid alterations per each 100 amino acids of the reference amino acid of the Ependymin polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least .90%, 95%, 96%, 97%, 98% or 99% identical to, for instance, the amino acid sequence shown in FIGS. 1A, 1B, and 1C (SEQ ID NO:2), the amino acid sequence encoded by deposited cDNA clone HDPIE88, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty-1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Ependymin protein expression as described below or as agonists and antagonists capable of enhancing or inhibiting Ependymin protein function. Further, such polypeptides can be used in the yeast two-hybrid system to "capture" Ependymin protein binding proteins which are also candidate agonists and antagonists according to the present invention. The yeast two hybrid system is described by Fields and Song (*Nature* 340:245–246 (1989)).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660–666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate Ependymin-specific antibodies include: a polypeptide comprising amino acid residues from about Ala-1 to about Gln-9 in SEQ ID NO:2; a polypeptide comprising amino acid residues from about Pro-8 to about Val-16 in SEQ ID NO:2; a polypeptide comprising amino acid residues from about Gln-19 to about Arg-27 in SEQ ID NO:2; a polypeptide comprising amino acid residues from about Ile-69 to about Ser-77 in SEQ ID NO:2; a polypeptide-comprising amino acid residues from about Asp-86 to about Glu-107 in SEQ ID NO:2; a polypeptide comprising amino acid residues from about Glu-113 to about Tyr-123 in SEQ ID NO:2; a polypeptide comprising amino acid residues from about Thr-131 to about Gln-139 in SEQ ID NO:2; a polypeptide comprising amino acid residues from about Leu-159 to about Phe-167 in SEQ ID NO:2; and a polypeptide comprising amino acid residues from about Leu-178 to about Ser-186 in SEQ ID NO:2. These polypeptide fragments have been determined to bear antigenic epitopes of the Ependymin protein by the analysis of the Jameson-Wolf antigenic index, as shown in FIG. 4 and Table I, above.

The epitope-bearing peptides and polypeptides of the invention may be produced by any conventional means (see, for example, Houghten, R. A., et al., *Proc. Natl. Acad. Sci. USA* 82:5131–5135 (1985); and U.S. Pat. No. 4,631,211 to Houghten, et al. (1986)).

Epitope-bearing peptides and polypeptides of the invention are used to induce antibodies according to methods well known in the art (see, for instance, Sutcliffe, et al., supra; Wilson, et al., supra; Chow, M., et al., *Proc. Natl. Acad. Sci. USA* 82:910–914; and Bittle, F. J., et al., *J. Gen. Virol.* 66:2347–2354 (1985)). Immunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, Ependymin polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric Ependymin protein or protein fragment alone (Fountoulakis, et al., *J. Biochem.* 270:3958–3964 (1995)).

Antibodies

Ependymin protein-specific antibodies for use in the present invention can be raised against the intact Ependymin protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to Ependymin protein. Fab and F(ab')2 fragments lack the Fc fragment of intact antibody, clear more rapidly from the circulation, and may have less non-specific tissue binding of an intact antibody (Wahl, et al., *J. Nucl. Meb.* 24:316–325 (1983)). Thus, these fragments are preferred.

The antibodies of the present invention may be prepared by any of a variety of methods. For example, cells expressing the Ependymin protein or an antigenic fragment thereof can be administered to an animal in order to induce the production of sera containing polyclonal antibodies. In a preferred method, a preparation of Ependymin protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Ependymin protein binding fragments thereof). Such monoclonal antibodies can be prepared using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in: *Monoclonal Antibodies and T-Cell Hybridomas*, Elsevier, N.Y., (1981) pp. 563–681)). In general, such procedures involve immunizing an animal (preferably a mouse) with a Ependymin protein antigen or, more preferably, with a Ependymin protein-expressing cell. Suitable cells can be recognized by their capacity to bind anti-Ependymin protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 µg/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Manassas, Va. After fusion, the resulting hybridoma cells are selectively maintained in HAT medium, and then cloned by limiting dilution as described by Wands and colleagues (*Gastroenterology* 80:225–232 (1981)). The hybridoma cells obtained through such a selection are then assayed to identify clones which secrete antibodies capable of binding the Ependymin protein antigen.

Alternatively, additional antibodies capable of binding to the Ependymin protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Ependymin protein-specific antibodies are used to immunize an animal, preferably a mouse. The splenocytes of such an animal are then used to produce hybridoma cells, and the hybridoma cells are screened to identify clones which produce an antibody whose ability to bind to the Ependymin protein-specific antibody can be blocked by the Ependymin protein antigen. Such antibodies comprise anti-idiotypic antibodies to the Ependymin protein-specific antibody and can be used to immunize an animal to induce formation of further Ependymin protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, Ependymin protein-binding fragments can be produced through the application of recombinant DNA technology or through synthetic chemistry.

For in vivo use of anti-Ependymin in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

Nervous System-Related Disorders

Diagnosis

The present inventors have discovered that Ependymin is expressed in primary dendritic cells, the KMH2 cell line, placenta, fetal and adult liver, spinal cord, osteoclastoma, cerebellum, synovial fibroblasts, 12 week old early stage human embryo, adrenal gland tumor, whole brain, Hodgkin's Lymphoma tissue, macrophages, HEL cell line, and chondrosarcoma. For a number of nervous system-related disorders, substantially altered (increased or decreased) levels of Ependymin gene expression can be detected in nervous system tissue or other cells or bodily fluids (e.g., sera, plasma, urine, synovial fluid or spinal fluid) taken from an individual having such a disorder, relative to a "standard" Ependymin gene expression level, that is, the Ependymin expression level in nervous system tissues or bodily fluids from an individual not having the nervous system disorder. Thus, the invention provides a diagnostic method useful during diagnosis of a nervous system disorder, which involves measuring the expression level of the gene encoding the Ependymin protein in nervous system tissue or other cells or body fluid from an individual and comparing the measured gene expression level with a standard Ependymin gene expression level, whereby an increase or decrease in the gene expression level compared to the standard is indicative of an nervous system disorder.

In particular, it is believed that certain tissues in mammals with cancer of the nervous express significantly reduced levels of the Ependymin protein and mRNA encoding the Ependymin protein when compared to a corresponding "standard" level. Further, it is believed that enhanced levels of the Ependymin protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a nervous system disorder, including cancers of this system, which involves measuring the expression level of the gene encoding the Ependymin protein in nervous system tissue or other cells or body fluid from an individual and comparing the measured gene expression level with a standard Ependymin gene expression level, whereby an increase or decrease in the gene expression level compared to the standard is indicative of a nervous system disorder.

Where a diagnosis of a disorder in the nervous system, including diagnosis of a tumor, has already been made according to conventional methods, the present invention is useful as a prognostic indicator, whereby patients exhibiting depressed Ependymin gene expression will experience a worse clinical outcome relative to patients expressing the gene at a level nearer the standard level.

By "assaying the expression level of the gene encoding the Ependymin protein" is intended qualitatively or quantitatively measuring or estimating the level of the Ependymin protein or the level of the mRNA encoding the Ependymin protein in a first biological sample either directly (e.g., by determining or estimating absolute protein level or mRNA level) or relatively (e.g., by comparing to the Ependymin protein level or mRNA level in a second biological sample). Preferably, the Ependymin protein level or mRNA level in the first biological sample is measured or estimated and compared to a standard Ependymin protein level or mRNA level, the standard being taken from a second biological sample obtained from an individual not having the disorder or being determined by averaging levels from a population of individuals not having a disorder of the nervous system. As will be appreciated in the art, once a standard Ependymin protein level or mRNA level is known, it can be used repeatedly as a standard for comparison.

By "biological sample" is intended any biological sample obtained from an individual, body fluid, cell line, tissue culture, or other source which contains Ependymin protein or mRNA. As indicated, biological samples include body fluids (such as sera, plasma, urine, synovial fluid and spinal fluid) which contain free Ependymin protein, nervous system tissue, and other tissue sources found to express complete or mature Ependymin or a Ependymin receptor. Methods for obtaining tissue biopsies and body fluids from mammals are well known in the art. Where the biological sample is to include mRNA, a tissue biopsy is the preferred source.

The present invention is useful for diagnosis or treatment of various nervous system-related disorders in mammals, preferably humans. Such disorders include any disregulations of nervous cell function including, but not limited to, Parkinson's disease, Alzheimer's disease, amyotrophic lateral sclerosis, pain, stroke, depression, anxiety, epilepsy, other neurological and psychiatric disorders, and the like.

Total cellular RNA can be isolated from a biological sample using any suitable technique such as the single-step guanidinium-thiocyanate-phenol-chloroform method described by Chomczynski and Sacchi (*Anal. Biochem.* 162:156–159 (1987)). Levels of mRNA encoding the Ependymin protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying Ependymin protein levels in a biological sample can occur using antibody-based techniques. For example, Ependymin protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting Ependymin protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I, carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying Ependymin protein levels in a biological sample obtained from an individual, Ependymin protein can also be detected in vivo by imaging. Antibody labels or markers for in vivo imaging of Ependymin protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A Ependymin protein-specific antibody or antibody fragment which has been labeled with an appropriate detectable imaging moiety, such as a radioisotope (for example, 131I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain Ependymin protein. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Treatment

As noted above, Ependymin polynucleotides and polypeptides are useful for diagnosis of conditions involving abnormally high or low expression of Ependymin activities. Given the cells and tissues where Ependymin is expressed as well as the activities modulated by Ependymin, it is readily apparent that a substantially altered (increased or decreased) level of expression of Ependymin in an individual compared to the standard or "normal" level produces pathological conditions related to the bodily system(s) in which Ependymin is expressed and/or is active.

It is well-known in the art that, in addition to a specific cellular function, cellular receptor molecules may also often be exploited by a virus as a means of initiating entry into a potential host cell. For example, it was recently discovered by Wu and colleagues (*J. Exp. Med.* 185:1681–1691 (1997)) that the cellular chemokine receptor CCR5 functions not only as a cellular chemokine receptor, but also as a receptor for macrophage-tropic human immunodeficiency virus (HIV)-1. In addition, RANTES, MIP-1a, and MIP-1b, which are agonists for the cellular chemokine receptor CCR5, inhibit entry of various strains of HIV-1 into susceptible cell lines (Cocchi, F., et al., *Science* 270:1811–1815 (1995)). Thus, the invention also provides a method of treating an individual exposed to, or infected with, a virus through the prophylactic or therapeutic administration of Ependymin, or an agonist or antagonist thereof, to block or disrupt the interaction of a viral particle with the Ependymin receptor and, as a result, block the initiation or continuation of viral infectivity.

The Ependymin of the present invention binds to the Ependymin receptor and, as such, is likely to block neurotropic viral infections. Further, Ependymin expression is also observed in many bone and cartilage tissues, and, as such, Ependymin is also likely to block initiation of infectious cycle of many viruses which infect bone or cartilage. More specifically, a non-limiting list of viruses whose infectious life cycles may be altered by Ependymin includes retroviruses such as HIV-1, HIV-2, human T-cell lymphotropic virus (HTLV)-1, and HTLV-1, as well as other DNA and RNA viruses including herpes simplex virus (HSV)-1, HSV-2, HSV-6, cytomegalovirus (CMV), Epstein-Barr virus (EBV), herpes samirii, adenoviruses, rhinoviruses, influenza viruses, reoviruses, and the like.

The ability of Ependymin of the present invention, or agonists or antagonists thereof, to prophylactically or therapeutically block viral infection may be easily tested by the skilled artisan. For example, Simmons and coworkers (Science 276:276–279 (1997)) and Arenzana-Seisdedos and colleagues (*Nature* 383:400 (1996)) each outline a method of observing suppression of HIV-1 infection by an antagonist of the CCR5 chemokine receptor and of the CC chemokine RANTES, respectively, in cultured peripheral blood mononuclear cells. Cells are cultured and infected with a virus, HIV-1 in both cases noted above. An agonist or antagonist of the CC chemokine or its receptor is then immediately added to the culture medium. Evidence of the ability of the agonist or antagonist of the chemokine or cellular receptor is determined by evaluating the relative success of viral infection at 3, 6, and 9 days post infection.

Administration of a pharmaceutical composition comprising an amount of an isolated Ependymin, or an agonist or antagonist thereof, of the invention to an individual either infected with a virus or at risk for infection with a virus is performed as described below.

It will also be appreciated by one of ordinary skill that, since the Ependymin protein of the invention is a member of the ependymin polypeptide family, the mature secreted form of the protein may be released in soluble form from the cells which express the Ependymin by proteolytic cleavage. Therefore, when Ependymin mature form is added from an exogenous source to cells, tissues or the body of an individual, the protein will exert its physiological activities on its target cells of that individual.

Therefore, it will be appreciated that conditions caused by a decrease in the standard or normal level of Ependymin activity in an individual, particularly disorders of the nervous system, can be treated by administration of Ependymin polypeptide (in the form of the mature protein). Thus, the invention also provides a method of treatment of an individual in need of an increased level of Ependymin activity comprising administering to such an individual a pharmaceutical composition comprising an amount of an isolated Ependymin polypeptide of the invention, particularly a mature form of the Ependymin protein of the invention, effective to increase the Ependymin activity level in such an individual.

Ependymin is found bound to collagen fibrils in the extracellular space of the mammalian leptomeninges. Ependymin, or agonists or antagonists thereof, may thus be employed in the treatment of ependymitis or other inflammation of the cellular membrane lining the central canal of the spinal cord and the brain ventricles. Ependymin is also found in collagen fibrils covering the endothelial cells of numerous blood vessels. Similarly, Ependymin, or agonists or antagonists thereof, may be used to regulate angiogenesis, and other processes or disorders which involve the formation, maintenance or disorganization of blood vessels, and to treat a variety of cancers which involve the formation of new blood vessels. A list of such cancers may include, but is not limited by, breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like.

Ependymins and other antiadhesive extracellular matrix proteins are involved in the mechanism whereby meningeal cells influence endfdot formation of Bergmann glial cells, which organize the superficial glia limitans surrounding the CNS. This function is essential in establishing accurate early development of the CNS and, as such, Ependymin of the present invention, or agonists or antagonists thereof, may be used to treat developmental disorders of the CNS and the brain. Ependymin may also be used to treat additional neurodegenerative disorders (such as Alzheimer's disease, Parkinson's disease, Amyotrophic lateral sclerosis, Retinitis pigmentosa, Cerebellar degeneration, and the like. Further, Ependymin of the present invention, or agonists or antagonists thereof, may be used to modulate long-term memory consolidation.

Ependymin of the present invention, or agonists or antagonists thereof, may be used to enhance the regeneration of the optic or other nerves. Several scientific studies have revealed that goldfish ependymin expression increases during optic nerve regeneration and that anti-ependymin antibodies can prevent the sharpening of the regenerating retinotectal projection (Schmidt, R. and Shashoua, V. E. *J. Neurochem.* 36:1368–1377 (1988); Thomodsson, F. R., et al., *Exp. Neurol.* 117:260–268 (1992)).

Ependymin of the present invention, or agonists or antagonists thereof, may be used to treat disorders resulting from axon ingrowth, for example, along blood vessels or into the meninx, or prophylactically, to prevent undesired or incorrect neuronal growth.

Ependymin of the present invention, or agonists or antagonists thereof, may be used to treat disorders of the blood-brain barrier since ependymin participates in the endothelial cell barrier by modulating cell-matrix interactions.

Formulations

The Ependymin polypeptide composition will be formulated and dosed in a fashion consistent with good medical practice, taking into account the clinical condition of the individual patient (especially the side effects of treatment with Ependymin polypeptide alone), the site of delivery of the Ependymin polypeptide composition, the method of administration, the scheduling of administration, and other factors known to practitioners. The "effective amount" of Ependymin polypeptide for purposes herein is thus determined by such considerations.

As a general proposition, the total pharmaceutically effective amount of Ependymin polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Ependymin polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the Ependymin of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The Ependymin polypeptide is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919,EP 58,481), copolymers of L-glutamic acid and gamma-ethyl-L-glutamate (Sidman, U., et al., *Biopolymers* 22:547–556 (1983)), poly (2–hydroxyethyl methacrylate; Langer, R., et al., *J. Biomed. Mater. Res.* 15:167–277 (1981), and Langer, R., *Chem. Tech.* 12:98–105 (1982)), ethylene vinyl acetate (Langer, R., et al., Id.) or poly-D- (-)-3-hydroxybutyric acid (EP 133,988). Sustained-release Ependymin polypeptide compositions also include liposomally entrapped Ependymin polypeptide. Liposomes containing Ependymin polypeptide are prepared by methods known in the art (DE 3,218,121; Epstein, et al., *Proc. Natl. Acad. Sci. (USA)* 82:3688–3692 (1985); Hwang, et al., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal Ependymin polypeptide therapy.

For parenteral administration, in one embodiment, the Ependymin polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Ependymin polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Ependymin polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Ependymin polypeptide salts.

Ependymin polypeptide to be used for therapeutic administration must be sterile. Sterility is readily accomplished by filtration through sterile filtration membranes (e.g., 0.2 micron membranes). Therapeutic Ependymin polypeptide compositions generally are placed into a container having a sterile access port, for example, an intravenous solution bag or vial having a stopper pierceable by a hypodermic injection needle.

Ependymin polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Ependymin polypeptide solution, and the resulting mixture is lyophilized. The infusion solution is prepared by reconstituting the lyophilized Ependymin polypeptide using bacteriostatic water-for-injection (WFI).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of Ependymin on cells, such as its interaction with Ependymin-binding molecules such as receptor molecules. An agonist is a compound which increases the natural biological functions of Ependymin or which functions in a manner similar to Ependymin, while antagonists decrease or eliminate such functions.

In another aspect of this embodiment the invention provides a method for identifying a receptor protein or other ligand-binding protein which binds specifically to a Ependymin polypeptide. For example, a cellular compartment, such as a membrane or a preparation thereof, may be prepared from a cell that expresses a molecule that binds Ependymin. The preparation is incubated with labeled Ependymin and complexes of Ependymin bound to the receptor or other binding protein are isolated and characterized according to routine methods known in the art. Alternatively, the Ependymin polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds Ependymin, such as a molecule of a signaling or regulatory pathway modulated by Ependymin. The preparation is incubated with labeled Ependymin in the absence or the presence of a candidate molecule which may be a Ependymin agonist or antagonist. The ability of the candidate molecule to bind the binding molecule is reflected in decreased binding of the labeled ligand. Molecules which bind gratuitously, i.e., without inducing the effects of Ependymin on binding the Ependymin binding molecule, are most likely to be good antagonists. Molecules that bind well and elicit effects that are the same as or closely related to Ependymin are agonists.

Ependymin-like effects of potential agonists and antagonists may by measured, for instance, by determining activity of a second messenger system following interaction of the candidate molecule with a cell or appropriate cell preparation, and comparing the effect with that of Ependymin or molecules that elicit the same effects as Ependymin. Second messenger systems that may be useful in this regard include but are not limited to AMP guanylate cyclase, ion channel or phosphoinositide hydrolysis second messenger systems.

Another example of an assay for Ependymin antagonists is a competitive assay that combines Ependymin and a potential antagonist with membrane-bound Ependymin receptor molecules or recombinant Ependymin receptor molecules under appropriate conditions for a competitive inhibition assay. Ependymin can be labeled, such as by radioactivity, such that the number of Ependymin molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Ependymin-induced activities, thereby preventing the action of Ependymin by excluding Ependymin from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Ependymin. The antisense RNA oligonucleotide hybridizes to the mRNA in vivo and blocks translation of the mRNA molecule into Ependymin polypeptide. The oligonucleotides described above can also be delivered to cells such that the antisense RNA or DNA may be expressed in vivo to inhibit production of Ependymin protein.

The agonists and antagonists may be employed in a composition with a pharmaceutically acceptable carrier, e.g., as described above.

The antagonists may be employed for instance to inhibit the formation of Ependymin-collagen fibrils which typically cover the endothelial cells of numerous blood vessels. As a result, anti-Ependymin antibodies may be used to regulate angiogenesis, and other processes or disorders which involve the formation, maintenance or disorganization of blood vessels, and to treat a variety of cancers which involve the formation of new blood vessels. Antibodies against Ependymin may also be employed to bind to and inhibit Ependymin activity to treat Parkinson's disease, Alzheimer's disease, amyotrophic lateral sclerosis, pain, stroke, depression, anxiety, epilepsy, and other neurological and psychiatric disorders. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Ependymin protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp (for a review of this technique, see Verma, et al., *Human Chromosomes: A Manual Of Basic Techniques*, Pergamon Press, New York (1988)).

Once a sequence has been mapped to a precise chromosomal location, the physical position of the sequence on the chromosome can be correlated with genetic map data. Such data are found, for example, on the World Wide Web (McKusick, V. *Mendelian Inheritance In Man*, available on line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "His-tagged" Ependymin in *E. coli*

The novel pHE4 series of bacterial expression vectors, in particular, the pHE4-5 vector may be used for bacterial expression in this example. pHE4-5/MPIFD23 vector plasmid DNA contains an insert which encodes another ORF. The construct was deposited with the American Type Culture Collection, 10801 University Boulevard, Manassas, Va. 20110-2209, on Sep. 30, 1997 and given Accession No.

209311. Using the NdeI and Asp 718 restriction sites flanking the irrelevant MPIF ORF insert, the pHE4-5 is linearized and the MPIF ORF is removed.

The pHE4-5 bacterial expression vector includes a neomycin phosphotransferase gene for selection, an *E. coli* origin of replication, a T5 phage promoter sequence, two lac operator sequences, a Shine-Dalgarno sequence, and the lactose operon repressor gene (lacIq). These elements are arranged such that an inserted DNA fragment encoding a polypeptide expresses that polypeptide with the six His residues (i.e., a "6xHis tag") covalently linked to the amino terminus of that polypeptide. The promoter and operator sequences of the pHE4-5 vector were made synthetically. Synthetic production of nucleic acid sequences is well known in the art (CLONETECH 95/96 Catalog, pages 215–216, CLONETECH, 1020 East Meadow Circle, Palo Alto, Calif. 94303).

The DNA sequence encoding the desired portion of the Ependymin protein comprising the mature form of the Ependymin amino acid sequence is amplified from the deposited cDNA clone using PCR oligonucleotide primers which anneal to the amino terminal sequences of the desired portion of the Ependymin protein and to sequences in the deposited construct 3' to the cDNA coding sequence. Additional nucleotides containing restriction sites to facilitate cloning in the pHE4-5 vector are added to the 5' and 3' primer sequences, respectively.

For cloning the mature form of the Ependymin protein, the 5' primer has the sequence 5' GCG <u>CAT ATG</u> GCC CCG CGC CCG TGC 3' (SEQ ID NO:8) containing the underlined NdeI restriction site followed by 15 nucleotides of the amino terminal coding sequence of the mature Ependymin sequence in SEQ ID NO:2. One of ordinary skill in the art would appreciate, of course, that the point in the protein coding sequence where the 5' primer begins may be varied to amplify a DNA segment encoding any desired portion of the complete Ependymin protein shorter or longer than the mature form of the protein. The 3' primer has the sequence 5' GCG <u>GGT ACC</u> TCA CCA GGA GCA GTC TTC GC 3' (SEQ ID NO:9) containing the underlined Asp 718 restriction site followed by 20 nucleotides complementary to the 3' end of the coding sequence of the Ependymin DNA sequence in FIGS. 1A, 1B, and 1C.

The amplified Ependymin DNA fragment and the vector pHE4-5 are digested with NdeI and Asp 718 and the digested DNAs are then ligated together. Insertion of the Ependymin DNA into the restricted pHE4-5 vector places the Ependymin protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Laboratory Manual, 2nd Ed.*; Cold Spring Harbor Laboratory Press, Cold Spring Harbor, N.Y. (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing Ependymin protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("EPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the Ependymin is loaded onto a nickel-nitrilo-tri-acetic acid ("Ni-NTA") affinity resin column (QIAGEN, Inc., supra). Proteins with a 6xHis tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the Ependymin is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH 6 buffer plus 200 mM NaCl. The purified protein is stored at 4° C. or frozen at −80° C.

The following alternative method may be used to purify Ependymin expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the Ependymin polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded Ependymin polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the Ependymin polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 MM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the Ependymin polypeptide (determined, for instance, by 16% SDS-PAGE) are then pooled.

The resultant Ependymin polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of Ependymin Protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature Ependymin protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (AcMNPV) followed by convenient restriction sites such as BamHI, XbaI and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, by Luckow and coworkers (*Virology* 170:31–39 (1989)).

The cDNA sequence encoding the full length Ependymin protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' GAT CGC <u>TCT AGA</u> TCC GCC ACC ATG CCA GGA CGC GCT CCC CTC CGC ACC GTC 3' (SEQ ID NO:10) containing the underlined XbaI restriction enzyme site, an efficient signal for initiation of translation in eukaryotic cells (Kozak, M., *J. Mol. Biol.* 196:947–950 (1987)), followed by 27 of nucleotides of the sequence of the complete Ependymin protein shown in FIGS. 1A, 1B, and 1C, beginning with the AUG initiation codon. The 3' primer has the sequence 5' GAT CGC <u>GGT ACC</u> TTA TCA CCA GGA GCA GTC TTC GCT CAT CTT CTC CAG 3' (SEQ ID NO:11) containing the underlined Asp 718 restriction site followed by 30 nucleotides complementary to the 3' noncoding sequence in FIGS. 1A, 11B, and 1C.

The amplified fragment is isolated from a 1% agarose gel using a commercially available kit ("Geneclean," BIO 101 Inc., La Jolla, Calif.). The fragment then is digested with XbaI and Asp 718 and again is purified on a 1% agarose gel. This fragment is designated herein F1.

The plasmid is digested with the restriction enzymes XbaI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human Ependymin gene by digesting DNA from individual colonies using XbaI and Asp 718 and then analyzing the digestion product by gel electrophoresis. The sequence of the cloned fragment is confirmed by DNA sequencing. This plasmid is designated herein pA2Ependymin.

Five μg of the plasmid pA2Ependymin is co-transfected with 1.0 μg of a commercially available linearized baculovirus DNA ("BaculoGold™ baculovirus DNA", Pharmingen, San Diego, Calif.), using the lipofection method described by Felgner and colleagues (*Proc. Natl. Acad. Sci. USA* 84:7413–7417 (1987)). One μg of BaculoGold™ virus DNA and 5 μg of the plasmid pA2Ependymin are mixed in a sterile well of a microtiter plate containing 50 μl of serum-free Grace's medium (Life Technologies Inc., Frederick, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (Life Technologies Inc., Frederick, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Frederick, Md., page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Ependymin.

To verify the expression of the Ependymin gene Sf9 cells are grown in Grace's medium supplemented with 10% heat-inactivated FBS. The cells are infected with the recombinant baculovirus V-Ependymin at a multiplicity of infection ("MOI") of about 2. If radiolabeled proteins are desired, 6 hours later the medium is removed and is replaced with SF900 II medium minus methionine and cysteine (available from Life Technologies Inc., Frederick, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the Ependymin protein and thus the cleavage point and length of the naturally associated secretory signal peptide.

Example 3

Cloning and Expression of Ependymin in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy, et al., *Biochem J.* 227:277–279 (1991); Bebbington, et al., *Biol/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen, et al., *Mol. Cel. Biol.* 5:438–447 (1985)) plus a fragment of the CMV-enhancer (Boshart, et al., *Cell* 41:521–530 (1985)). Multiple cloning sites, e.g., with the restriction enzyme cleavage sites BamHI, XbaI and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pEpendyminHA, is made by cloning a portion of the cDNA encoding the complete Ependymin protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete Ependymin polypeptide is cloned into the polylinker region of the vector so that recombinant protein expression is directed by the CMV promoter. The plasmid construction strategy is as follows. The Ependymin cDNA of the deposited clone is amplified using primers that contain convenient restriction sites, much as described above for construction of vectors for expression of Ependymin in *E. coli*. Suitable primers include the following, which are used in this example. The 5' primer, containing the underlined Asp 718 site, a Kozak sequence, an AUG start codon, a sequence, and 24 nucleotides of the 5' coding region of the complete Ependymin polypeptide, has the following sequence: 5' GAT CGC <u>GGT ACC</u> GCC ATC ATG CCA GGA CGC GCT CCC CTC CGC 3' (SEQ ID NO:12). The 3' primer, containing the underlined BamHI and 20 of nucleotides complementary to the 3' coding sequence immediately before the stop codon, has the following sequence: 5' GAT CGC GGA TCC TCA CCA GGA GCA GTC TTC GC 3' (SEQ ID NO:13).

The PCR amplified DNA fragment and the vector, pcDNAI/Amp, are digested with Asp 718 and BamHI and then ligated. The ligation mixture is transformed into E. E. coli strain SURE (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete Ependymin polypeptide.

For expression of recombinant Ependymin, COS cells are transfected with an expression vector, as described above, using DEAE-dextran, as described, for instance, by Sambrook and coworkers (*Molecular Cloning: a Laboratory Manual*, Cold Spring Laboratory Press, Cold Spring Harbor, N.Y. (1989)). Cells are incubated under conditions for expression of Ependymin by the vector.

Expression of the Ependymin-HA fusion protein is detected by radiolabeling and immunoprecipitation, using methods described in, for example Harlow and colleagues (*Antibodies: A Laboratory Manual*, 2nd Ed.; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer:150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of Ependymin polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357–1370 (1978); Hamlin, J. L. and Ma, C. *Biochem. et Biophys. Acta*, 1097:107–143 (1990); Page, M. J. and Sydenham, M. A. *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438–447 (1985)) plus a fragment isolated from the enhancer of the immediate early gene of human cytomegalovirus (CMV; Boshart, et al., *Cell* 41:521–530 (1985)). Downstream of the promoter are the following single restriction enzyme cleavage sites that allow the integration of the genes: BamHI, XbaI, and Asp 718. Behind these cloning sites the plasmid contains the 3' intron and polyadenylation site of the rat preproinsulin gene. Other high efficiency promoters can also be used for the expression, e.g., the human B-actin promoter, the SV40 early or late promoters or the long terminal repeats from other retroviruses, e.g., HIV and HTLVI. Clontech's Tet-Off and Tet-On gene expression systems and similar systems can be used to express the Ependymin polypeptide in a regulated way in mammalian cells (Gossen, M., and Bujard, H. *Proc. Natl. Acad. Sci. USA* 89:5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes XbaI and Asp 718 and then dephosphorylated using calf intestinal phosphates by procedures known in the art. The vector is then isolated from a 1% agarose gel.

The DNA sequence encoding the complete Ependymin polypeptide is amplified using PCR oligonucleotide primers corresponding to the 5' and 3' sequences of the desired portion of the gene. The 5' primer containing the underlined XbaI site, a Kozak sequence (in italics), an AUG start codon, and 30 nucleotides of the 5' coding region of the complete Ependymin polypeptide, has the following sequence: 5' GAT CGC TCT AGA TCC GCC *ACCATG* CCA GGA CGC GCT CCC CTC CGC ACC GTC 3' (SEQ ID NO:14). The 3' primer, containing the underlined Asp 718 and 30 of nucleotides complementary to the 3' coding sequence immediately before the stop codon as shown in FIGS. 1A, 1B, and 1C (SEQ ID NO:1), has the sequence shown in the above example as SEQ ID NO:11.

The amplified fragment is digested with the endonucleases XbaI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using lipofectin (Felgner, et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μμM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of Ependymin mRNA Expression

Northern blot analysis is carried out to examine Ependymin gene expression in human tissues, using methods described by, among others, Sambrook and colleagues (supra). A cDNA probe containing the entire nucleotide sequence of the Ependymin protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for Ependymin mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT 1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listing submitted with U.S. application Ser. No. 09/229,583, filed on Jan. 13, 1999,the Sequence Listing submitted with U.S. Provisional Application Serial No. 60/071,330, filed on Jan. 14, 1998, and the Sequence Listing submitted with U.S. Provisional Application Serial No. 60/075,278, filed on Feb. 19, 1998 (to both of which the present application claims benefit of the filing date under 35 U.S.C. §119(e)), in both computer and paper forms are hereby incorporated by reference in their entireties.

What is claimed is:

1. An isolated protein comprising an amino acid sequence selected from the group consisting of:
 (a) amino acid residues −37 to +187 of SEQ ID NO:2;
 (b) amino acid residues −36 to +187 of SEQ ID NO:2; and
 (c) amino acid residues +1 to +187 of SEQ ID NO:2.

2. The protein of claim 1, wherein the amino acid sequence is (a).

3. The protein of claim 1, wherein the amino acid sequence is (b).

4. The protein of claim 1, wherein the amino acid sequence is (c).

5. The protein of claim 1, wherein the amino acid sequence further comprises a heterologous polypeptide.

6. The protein of claim 5, wherein the heterologous polypeptide is the Fc domain of immunoglobulin.

7. The protein of claim 1, wherein said protein is glycosylated.

8. The protein of claim 1, wherein said protein is fused to polyethylene glycol.

9. An isolated protein produced by a method comprising:
(a) expressing the protein of claim 1 by a cell; and
(b) recovering the protein.

10. A composition comprising the protein of claim 1 and a carrier.

11. An isolated protein comprising an amino acid sequence selected from the group consisting of:
(a) the amino acid sequence of the full-length polypeptide encoded by the cDNA in American Type Culture Collection Deposit No. 209464;
(b) the amino acid sequence of the full-length polypeptide, excluding the N-terminal methionine residue, encoded by the cDNA in American Type Culture Collection Deposit No. 209464; and
(c) the amino acid sequence of the mature polypeptide encoded by the cDNA in American Type Culture Collection Deposit No. 209464.

12. The protein of claim 11, wherein the amino acid sequence is (a).

13. The protein of claim 11, wherein the amino acid sequence is (b).

14. The protein of claim 11, wherein the amino acid sequence is (c).

15. The protein of claim 11 wherein the amino acid sequence further comprises a heterologous polypeptide.

16. The protein of claim 15 wherein the heterologous polypeptide is the Fc domain of immunoglobulin.

17. The protein of claim 11 wherein said protein is glycosylated.

18. The protein of claim 11 wherein said protein is fused to polyethylene glycol.

19. An isolated protein produced by a method comprising:
(a) expressing the protein of claim 11 by a cell; and
(b) recovering the protein.

20. A composition comprising the protein of claim 11 and a carrier.

21. An isolated protein comprising a first amino acid sequence 90% or more identical to a second amino acid sequence selected from the group consisting of:
(a) amino acid residues −37 to +187 of SEQ ID NO:2;
(b) amino acid residues −11 to +187 of SEQ ID NO:2; and
(c) amino acid residues +1 to +187 of SEQ ID NO:2.

22. The protein of claim 21 wherein the first amino acid sequence is 90% or more identical to the second amino acid sequence (a).

23. The protein of claim 21 wherein the first amino acid sequence is 90% or more identical to the second amino acid sequence (b).

24. The protein of claim 21 wherein the first amino acid sequence is 90% or more identical to the second amino acid sequence (c).

25. The protein of claim 21 wherein the first amino acid sequence is 95% or more identical to the second amino acid sequence (a).

26. The protein of claim 21 wherein the first amino acid sequence is 95% or more identical to the second amino acid sequence (b).

27. The protein of claim 21 wherein the first amino acid sequence is 95% or more identical to the second amino acid sequence (c).

28. The protein of claim 21 wherein the amino acid sequence further comprises a heterologous polypeptide.

29. The protein of claim 28 wherein the heterologous polypeptide is the Fc domain of immunoglobulin.

30. The protein of claim 21 wherein said protein is glycosylated.

31. The protein of claim 21 wherein said protein is fused to polyethylene glycol.

32. An isolated protein produced by a method comprising:
(a) expressing the protein of claim 21 by a cell; and
(b) recovering the protein.

33. A composition comprising the protein of claim 21 and a carrier.

34. An isolated protein comprising a first amino acid sequence 90% or more identical to a second amino acid sequence selected from the group consisting of:
(a) the amino acid sequence of the full-length polypeptide encoded by the cDNA in American Type Culture Collection Deposit No. 209214;
(b) the amino acid sequence of the full-length polypeptide, excluding the N-Terminal methionine residue, encoded by the cDNA in American Type Culture Collection Deposit No. 209214; and
(c), the amino acid sequence of the mature polypeptide encoded by the cDNA in American Type Culture Collection Deposit No. 209214.

35. The protein of claim 34 wherein the first amino acid sequence is 90% or more identical to the second amino acid sequence (a).

36. The protein of claim 34 wherein the first amino acid sequence is 90% or more identical to the second amino acid sequence (b).

37. The protein of claim 34 wherein the first amino acid sequence is 90% or more identical to the second amino acid sequence (c).

38. The protein of claim 34 wherein the first amino acid sequence is 95% or more identical to the second amino acid sequence (a).

39. The protein of claim 34 wherein the first amino acid sequence is 95% or more identical to the second amino acid sequence (b).

40. The protein of claim 34 wherein the first amino acid sequence is 95% or more identical to the second amino acid sequence (c).

41. The protein of claim 34 wherein the amino acid sequence further comprises a heterologous polypeptide.

42. The protein of claim 41 wherein the heterologous polypeptide is the Fc domain of immunoglobulin.

43. The protein of claim 41 wherein said protein is glycosylated.

44. The protein of claim 34 wherein said protein is fused to polyethylene glycol.

45. An isolated protein produced by a method comprising:
(a) expressing the protein of claim 34 by a cell; and
(b) recovering the protein.

46. A composition comprising the protein of claim 34 and a carrier.

47. An isolated protein comprising an amino acid sequence selected from the group consisting of:
(a) amino acid residues $n^1$ to +187 of SEQ ID NO:2, where $n^1$ is an integer from −37 to +4;
(b) amino acid residues −37 to $m^1$ of SEQ ID NO:2, where $m^1$ is an integer from +173 to +187; and
(c) amino acid residues $n^1$ to $m^1$ of SEQ ID NO:2, where $n^1$ is an integer from −37 to +4 and $m^1$ is an integer in the range of +173 to +187.

48. The protein of claim 47, wherein said amino acid sequence is (a).

49. The protein of claim 47, wherein said amino acid sequence is (b).

50. The protein of claim 47 wherein said amino acid sequence is (c).

51. The protein of claim 48, wherein said amino acid sequence comprises amino acid residues +4 to +187 of SEQ ID NO:2.

52. The isolated protein of claim 49, wherein said amino acid sequence comprises amino acid residues −37 to +173 of SEQ ID NO:2.

53. The protein of claim 50, wherein said amino acid sequence comprises amino acid residues +4 to +173 of SEQ ID NO:2.

54. The protein of claim 47 wherein the amino acid sequence further comprises a heterologous polypeptide.

55. The protein of claim 54 wherein the heterologous polypeptide is the Fc domain of immunoglobulin.

56. The protein of claim 47 wherein said protein is glycosylated.

57. The protein of claim 47 wherein said protein is fused to polyethylene glycol.

58. An isolated protein produced by a method comprising:
   (a) expressing the protein of claim 47 by a cell; and
   (b) recovering the protein.

59. A composition comprising the protein of claim 47 and a carrier.

60. An isolated protein comprising an amino acid sequence selected from the group consisting of:
   (a) amino acid residues 1 to 9 of SEQ ID NO:2;
   (b) amino acid residues 8 to 16 of SEQ ID NO:2;
   (c) amino acid residues 19 to 27 of SEQ ID NO:2;
   (d) amino acid residues 69 to 77 of SEQ ID NO:2;
   (e) amino acid residues 86 to 107 of SEQ ID NO:2;
   (f) amino acid residues 113 to 123 of SEQ ID NO:2;
   (g) amino acid residues 131 to 139 of SEQ ID NO:2;
   (h) amino acid residues 159 to 167 of SEQ ID NO:2; and
   (i) a fragment of amino acid residues −37 to +187 of SEQ ID NO:2 wherein the fragment binds calcium.

61. The protein of claim 60, wherein said amino acid sequence is a).

62. The protein of claim 60, wherein said amino acid sequence is (b).

63. The protein of claim 60, wherein said amino acid sequence is (c).

64. The protein of claim 60, wherein said amino acid sequence is (d).

65. The protein of claim 60, wherein said amino acid sequence is (e).

66. The protein of claim 60, wherein said amino acid sequence is (f).

67. The protein of claim 60, wherein said amino acid sequence is (g).

68. The protein of claim 60, wherein said amino acid sequence is (h).

69. The protein of claim 60, wherein said amino acid sequence is (i).

70. The protein of claim 60 wherein the amino acid sequence further comprises a heterologous polypeptide.

71. The protein of claim 70 wherein the heterologous polypeptide is the Fc domain of immunoglobulin.

72. The protein of claim 70 wherein said protein is glycosylated.

73. The protein of claim 60 wherein said protein is fused to polyethylene glycol.

74. An isolated protein produced by a method comprising:
   (a) expressing the protein of claim 60 by a cell; and
   (b) recovering the protein.

75. A composition comprising the protein of claim 60 and a carrier

76. An isolated protein comprising at least 30 contiguous amino acid residues of SEQ ID NO:2.

77. The protein of claim 76 wherein the protein comprises at least 50 contiguous amino acid residues of SEQ ID NO:2.

78. The protein of claim 76 wherein the amino acid sequence further comprises a heterologous polypeptide.

79. The protein of claim 78 wherein the heterologous polypeptide is the Fc domain of immunoglobulin.

80. The protein of claim 78 wherein said protein is glycosylated.

81. The protein of claim 76 wherein said protein is fused to polyethylene glycol.

82. An isolated protein produced by a method comprising:
   (a) expressing the protein of claim 76 by a cell; and
   (b) recovering the protein.

83. A composition comprising the protein of claim 76 and a carrier.

84. An isolated protein comprising at least 30 contiguous amino acid residues encoded by the cDNA in American Type Culture Collection Deposit No. 209214.

85. The protein of claim 84 wherein the protein comprises at least 50 contiguous amino acid residues encoded by the cDNA in American Type Culture Collection Deposit No. 209214.

86. The protein of claim 84 wherein the amino acid sequence further comprises a heterologous polypeptide.

87. The protein of claim 86 wherein the heterologous polypeptide is the Fc domain of immunoglobulin.

88. The protein of claim 84 wherein said protein is glycosylated.

89. The protein of claim 84 wherein said protein is fused to polyethylene glycol.

90. An isolated protein produced by a method comprising:
   (a) expressing the protein of claim 84 by a cell; and
   (b) recovering the protein.

91. A composition comprising the protein of claim 84 and a carrier.

* * * * *

UNITED STATES PATENT AND TRADEMARK OFFICE
CERTIFICATE OF CORRECTION

PATENT NO. : 6,683,161 B1
DATED : January 27, 2004
INVENTOR(S) : Ebner et al.

It is certified that error appears in the above-identified patent and that said Letters Patent is hereby corrected as shown below:

Title page,
Item [56], References Cited, "Genbank Accession No." reference, delete "Hillilier" and insert -- Hillier --;

Column 81,
Line 46, delete ""-11 to +187" and insert -- -36 to +187 --;

Column 82,
Lines 17, 22, and 25, delete "Deposit No. 209214" and insert -- Deposit No. 209464 --;

Column 83,
Line 42, delete "a)" and insert -- (a) --;

Column 84,
Line 16, insert a -- . -- after the word "carrier";
Lines 37 and 40, delete "Deposit No. 209214" and insert -- Deposit No. 209464 --.

Signed and Sealed this

Thirteenth Day of July, 2004

JON W. DUDAS
*Acting Director of the United States Patent and Trademark Office*

SEQUENCE LISTING

```
<160> NUMBER OF SEQ ID NOS: 20

<210> SEQ ID NO 1
<211> LENGTH: 2525
<212> TYPE: DNA
<213> ORGANISM: Homo sapiens
<220> FEATURE:
<221> NAME/KEY: CDS
<222> LOCATION: (296)..(970)
<223> OTHER INFORMATION:
<220> FEATURE:
<221> NAME/KEY: sig_peptide
<222> LOCATION: (296)..(406)
<223> OTHER INFORMATION:
<220> FEATURE:
<221> NAME/KEY: mat_peptide
<222> LOCATION: (407)..(967)
<223> OTHER INFORMATION:

<400> SEQUENCE: 1
ccacgcgtcc ggaaaaccga agcggcagaa ggcagtggca gcaggcagtg gcccaggcag        60
aaatagctcc cgcgcgattc actggagcct tccccgggcc ctggtcccgg ctaccgggac       120
tcgcgcgtcc ggatctcaaa agcggcagag gccaccgaag ggacaggaag cactttggtc       180
cagaccacac tcccggcaca gtgcggaaag agccggcggg agccactctg atcccggacg       240
cctcagcgcc cccttgggct tgggcttgcc ctcgggccgg ggaaggctga ccgcg atg        298
                                                                    Met cca gga cgc gct ccc ctc cgc acc gtc ccg ggc gcc ctg ggt gcc tgg        346
Pro Gly Arg Ala Pro Leu Arg Thr Val Pro Gly Ala Leu Gly Ala Trp
    -35                 -30                 -25 ctg ctg ggc ggc ctc tgg gcc tgg acc ctg tgc ggc ctg tgc agc ctg        394
Leu Leu Gly Gly Leu Trp Ala Trp Thr Leu Cys Gly Leu Cys Ser Leu
-20                 -15                 -10                  -5 ggg gcg gtg gga gcc ccg cgc ccg tgc cag gcg ccg cag cag tgg gag        442
Gly Ala Val Gly Ala Pro Arg Pro Cys Gln Ala Pro Gln Gln Trp Glu
```

|  |  |  |  |  |  |  |  |  |  |  |  |  |  |
|---|---|---|---|---|---|---|---|---|---|---|---|---|---|
|  | -1 | 1 |  |  | 5 |  |  |  |  | 10 |  |  |  |
| ggg | cgc | cag | gtt | atg | tac | cag | caa | agt | agc | ggg | cgc | aac | agc cgc gcc |
| Gly | Arg | Gln | Val | Met | Tyr | Gln | Gln | Ser | Ser | Gly | Arg | Asn | Ser Arg Ala |
|  |  | 15 |  |  |  |  | 20 |  |  |  |  | 25 |  |

490 ctg ctc tcc tac gac ggg ctc aac cag cgc gtg cgg gtg ctg gac gag       538
Leu Leu Ser Tyr Asp Gly Leu Asn Gln Arg Val Arg Val Leu Asp Glu
         30              35              40 agg aag gcg ctg atc ccc tgc aag aga tta ttt gaa tat att ttg ctg       586
Arg Lys Ala Leu Ile Pro Cys Lys Arg Leu Phe Glu Tyr Ile Leu Leu
 45              50              55                      60 tat aag gat gga gtg atg ttt cag att gac caa gcc acc aag cag tgc       634
Tyr Lys Asp Gly Val Met Phe Gln Ile Asp Gln Ala Thr Lys Gln Cys
                 65              70              75 tca aag atg acc ctg aca cag ccc tgg gat cct ctt gac att cct caa       682
Ser Lys Met Thr Leu Thr Gln Pro Trp Asp Pro Leu Asp Ile Pro Gln
         80              85              90 aac tcc acc ttt gaa gac cag tac tcc att ggg ggg cct cag gag cag       730
Asn Ser Thr Phe Glu Asp Gln Tyr Ser Ile Gly Gly Pro Gln Glu Gln
         95              100             105 atc acc gtc cag gag tgg tcg gac aga aag tca gct aga tcc tat gaa       778
Ile Thr Val Gln Glu Trp Ser Asp Arg Lys Ser Ala Arg Ser Tyr Glu
     110             115             120 acc tgg att ggc atc tat aca gtc aag gat tgc tat cct gtc cag gaa       826
Thr Trp Ile Gly Ile Tyr Thr Val Lys Asp Cys Tyr Pro Val Gln Glu
125             130             135             140 acc ttt acc ata aac tac agt gtg ata ttg tct acg cgg ttt ttt gac       874
Thr Phe Thr Ile Asn Tyr Ser Val Ile Leu Ser Thr Arg Phe Phe Asp
                 145             150             155 atc cag ctg ggt att aaa gac ccc tcg gtg ttt acc cct cca agc acg       922
Ile Gln Leu Gly Ile Lys Asp Pro Ser Val Phe Thr Pro Pro Ser Thr
         160             165             170 tgc cag atg gcc caa ctg gag aag atg agc gaa gac tgc tcc tgg           967
Cys Gln Met Ala Gln Leu Glu Lys Met Ser Glu Asp Cys Ser Trp
         175             180             185 tgagcctgtg catagggaag cggcagcatc ggatgtcagc ccctgcggc cccagctgga      1027 gatggatatg agactagtca agatgtgaat gctaattgga gagaaatata attttaggaa     1087
gatgcacatt gatgtggggt tttgatgtgt ctgattttga ctactcaagc tctgtttaca    1147
gaagaaaatt gaatggcgag ggtgtggcca tatgaactga ctagatggct aatatggaca    1207
ctttgggtat ttctaatgcc tgttcagggc tggttttctg catgcacggg tatacacata    1267
atgcagtgcc atgcacatag ggaagggtca gtaagagaag tttgccttgg cagcaagtat    1327
ttattgttga cattattcag aattagtgat aataaaaagc agagtgattt tggtcaattt    1387
tattattaat tcttaaattc cctgcagaga atgccccctt tattgctgca ccagggtggg    1447
cattgctccc actgagccct actccaccct gtccctgcac tcccttggtt gccaaaaaaa    1507
tgataactta aatcccttcc agacttaaga attttatggc atggcccaat tgatataaac    1567
atttagaagg aaatgaaaag ctaaatagg aagtaattat tcctctaaag aaacattttg     1627
agcaaggcag tttagagaat cctaatgtct acactggcat agcacgagcc atgtaagctt    1687 ctttttttc tatgcaagag tattgatgta tgtgctgaat cttcacagac ttgtcaatac     1747
acaggcagta ttctaaaata gcactgaaca gggagtcagg agactattgt ctcctaaacc    1807
caggactaga gttccctcgt actgtcactc ctttggtcat taaatgcact gggcttgccc    1867
gcactttggc cttcctagaa cgctgcttca taacctctct gtctgacttc tgcatctcct    1927
tccaggtcag ctcattcaca agagttgctc ccaagcctgg atgagttgca ccttgcatct    1987

-continued

```
tgagcatgca tttctcacaa taattattaa gctgtgtgat aatttctgct ttcaggacac    2047
tcatccatta tcttggctgt gagctccttg ggtacgggta ccttgtatgt ttaattttat    2107
atccctagca caaagcaagt gcctggcaca tagtcagtgc cctaagtatt tgtagagtga    2167
agaatgccag cctctcttgt ccctggtttc cttatgtgtt gaatgtggtt gagtttgtcc    2227
attgctaggg agagacttcc agtaataaaa tttactattc tagatgcttc tactgttatg    2287 tttatctgc ccatttatct ttcttagtta ccaggagaaa tgtgtgacac ctatattata     2347
atgaaaacaa tcttattact tatagtttat ctatattaaa caaatttaat tgcatttaaa    2407
gcattctttg atattgttgc ttttgcaata aatatggata atcttggtta taagggagtt    2467 aaacaatgc tgtaataaat aaagtgtttc atgtgatcaa aaaaaaaaa aaaaaaa        2525
```

<210> SEQ ID NO 2
<211> LENGTH: 224
<212> TYPE: PRT
<213> ORGANISM: Homo sapiens

<400> SEQUENCE: 2

```
Met Pro Gly Arg Ala Pro Leu Arg Thr Val Pro Gly Ala Leu Gly Ala
        -35             -30             -25

Trp Leu Leu Gly Gly Leu Trp Ala Trp Thr Leu Cys Gly Leu Cys Ser
    -20             -15             -10

Leu Gly Ala Val Gly Ala Pro Arg Pro Cys Gln Ala Pro Gln Gln Trp
 -5          -1   1               5                  10

Glu Gly Arg Gln Val Met Tyr Gln Gln Ser Ser Gly Arg Asn Ser Arg
            15                  20                  25

Ala Leu Leu Ser Tyr Asp Gly Leu Asn Gln Arg Val Arg Val Leu Asp
        30                  35                  40

Glu Arg Lys Ala Leu Ile Pro Cys Lys Arg Leu Phe Glu Tyr Ile Leu
    45                  50                  55

Leu Tyr Lys Asp Gly Val Met Phe Gln Ile Asp Gln Ala Thr Lys Gln
60                  65                  70                  75

Cys Ser Lys Met Thr Leu Thr Gln Pro Trp Asp Pro Leu Asp Ile Pro
                80                  85                  90

Gln Asn Ser Thr Phe Glu Asp Gln Tyr Ser Ile Gly Gly Pro Gln Glu
                95                 100                 105

Gln Ile Thr Val Gln Glu Trp Ser Asp Arg Lys Ser Ala Arg Ser Tyr
            110                 115                 120

Glu Thr Trp Ile Gly Ile Tyr Thr Val Lys Asp Cys Tyr Pro Val Gln
        125                 130                 135

Glu Thr Phe Thr Ile Asn Tyr Ser Val Ile Leu Ser Thr Arg Phe Phe
140                 145                 150                 155

Asp Ile Gln Leu Gly Ile Lys Asp Pro Ser Val Phe Thr Pro Pro Ser
                160                 165                 170

Thr Cys Gln Met Ala Gln Leu Gly Lys Met Ser Glu Asp Cys Ser Trp
            175                 180                 185
```

<210> SEQ ID NO 3
<211> LENGTH: 216
<212> TYPE: PRT
<213> ORGANISM: Carassius auratus

<400> SEQUENCE: 3

```
Met Met His Thr Val Lys Leu Leu Cys Val Val Phe Ser Cys Leu Cys
  1               5                  10                  15
```

```
Ala Val Ala Trp Ala Ser Ser Asp Arg Gln Pro Cys His Ser Pro Pro
             20                  25                  30

Leu Ile Ser Gly Thr Met Lys Val Val Ser Thr Gly Gly His Asp Leu
         35                  40                  45

Ala Ser Gly Glu Phe Ser Tyr Asp Ser Lys Ala Asn Lys Phe Arg Phe
     50                  55                  60

Val Glu Asp Ala Ala His Ala Asn Lys Thr Ser His Thr Asp Val Leu
 65                  70                  75                  80

Val His Phe Glu Glu Gly Thr Leu Tyr Glu Ile Asp Ser Lys Asn Glu
                 85                  90                  95

Ser Cys Lys Lys Glu Thr Leu Gln Phe Arg Lys His Leu Met Glu Ile
             100                 105                 110

Pro Pro Asp Ala Thr His Glu Ser Glu Ile Tyr Met Gly Ser Pro Ser
         115                 120                 125

Ile Thr Glu Gln Gly Leu Arg Val Arg Val Trp Ser Gly Lys Leu Pro
     130                 135                 140

Glu Leu His Ala His Tyr Ser Leu Ser Ile Thr Ser Cys Gly Cys Leu
145                 150                 155                 160

Pro Val Ser Gly Ser Tyr Tyr Gly Asp Lys Lys Asp Leu Leu Phe Ser
                165                 170                 175

Phe Phe Gly Val Glu Thr Glu Val Asp Asp Leu Gln Val Phe Val Pro
            180                 185                 190

Pro Ala Tyr Cys Glu Gly Val Ala Phe Glu Glu Ala Pro Asp Asp His
        195                 200                 205

Ser Phe Phe Asp Leu Phe His Asp
    210                 215

<210> SEQ ID NO 4
<211> LENGTH: 221
<212> TYPE: PRT
<213> ORGANISM: Oncorhynchus mykiss

<400> SEQUENCE: 4

Met Gln Asp Phe Ala Phe Ala Ala Leu Ser Ile Trp Leu Cys Leu Gly
 1               5                  10                  15

Ala Thr Ala Leu Ala Glu Ser His Gly Pro Gln His Cys Thr Ser Pro
             20                  25                  30

Asn Met Thr Gly Val Leu Thr Val Met Ala Leu Thr Gly Gly Glu Ile
         35                  40                  45

Lys Ala Thr Gly His Tyr Ser Tyr Asp Ser Thr Asn Lys Lys Leu Arg
     50                  55                  60

Phe Thr Glu Ser Glu Met His Leu Asn Lys Thr Glu His Leu Glu Asp
 65                  70                  75                  80

Tyr Leu Met Leu Phe Glu Glu Gly Val Phe Tyr Asp Ile Asp Met Lys
                 85                  90                  95

Asn Gln Ser Cys Lys Lys Met Ser Leu His Ser His Ala His Ala Leu
             100                 105                 110

Glu Leu Pro Ala Gly Ala Ala His Gln Val Glu Leu Phe Leu Gly Ser
         115                 120                 125

Asp Thr Val Gln Glu Asp Asn Ile Lys Val Asn Ile Trp Met Gly Ser
     130                 135                 140

Val Ala Glu Thr Lys Gly Gln Tyr Ser Ala Leu Thr Thr Val Gly Glu
145                 150                 155                 160

Cys Leu Pro Leu Ser Thr Phe Tyr Ser Thr Asp Ser Ile Thr Leu Leu
```

```
                    165                 170                 175
Phe Ser Asn Ser Glu Val Val Thr Glu Val Lys Ala Pro Glu Met Phe
                180                 185                 190

Thr Leu Pro Ser Phe Cys Glu Ala Val Glu Leu Glu Glu Thr Pro Lys
            195                 200                 205

Gly Gln Lys Asn Asp Phe Phe Asn Ile Phe Asn Thr Val
        210                 215                 220

<210> SEQ ID NO 5
<211> LENGTH: 215
<212> TYPE: PRT
<213> ORGANISM: Cyprinus carpio

<400> SEQUENCE: 5

Met His Thr Val Lys Leu Leu Cys Val Val Phe Ser Cys Leu Cys Ala
  1               5                  10                  15

Val Ala Trp Ala Ser Ser Asn Arg Gln Pro Cys His Ser Pro Pro Leu
                 20                  25                  30

Thr Ser Gly Thr Met Lys Val Val Ser Thr Gly Gly His Asp Leu Ala
             35                  40                  45

Ser Gly Glu Phe Ser Tyr Asp Ser Lys Ala Asn Lys Phe Arg Phe Val
         50                  55                  60

Glu Asp Thr Ala His Ala Asn Lys Thr Ser His Met Asp Val Leu Val
 65                  70                  75                  80

His Phe Glu Glu Gly Val Leu Tyr Glu Ile Asp Ser Lys Asn Glu Ser
                 85                  90                  95

Cys Lys Lys Glu Thr Leu Gln Phe Arg Lys His Leu Met Glu Ile Pro
                100                 105                 110

Pro Asp Ala Thr His Glu Ser Glu Ile Tyr Met Gly Ser Pro Ser Ile
            115                 120                 125

Thr Glu Gln Gly Leu Arg Val Arg Val Trp Asn Gly Lys Leu Pro Glu
        130                 135                 140

Leu His Ala His Tyr Ser Leu Ser Thr Thr Ser Cys Gly Cys Leu Pro
145                 150                 155                 160

Val Ser Gly Ser Tyr Tyr Gly Asp Lys Lys Asp Leu Leu Phe Ser Phe
                165                 170                 175

Phe Gly Val Glu Thr Glu Val Asp Asp Pro Gln Val Phe Val Pro Pro
            180                 185                 190

Ala Tyr Cys Glu Ala Val Ala Phe Glu Glu Ala Pro Asp Asp His Ser
        195                 200                 205

Phe Phe Asp Leu Phe His Asp
    210                 215

<210> SEQ ID NO 6
<211> LENGTH: 217
<212> TYPE: PRT
<213> ORGANISM: Danio rerio

<400> SEQUENCE: 6

Met His Thr Val Lys Leu Leu Cys Val Val Phe Ser Cys Leu Cys Ala
  1               5                  10                  15

Ile Gly Trp Ala Ser His His Ser His Arg Gln Pro Cys His Ser Pro
                 20                  25                  30

Gln Leu Thr Ser Gly Thr Met Lys Val Val Ser Thr Gly Gly His Asp
             35                  40                  45

Leu Ala Ser Gly Glu Phe Ser Tyr Asp Ser Lys Thr Asn Lys Phe Arg
```

```
            50                  55                  60
Phe Val Glu Asp Thr Thr His Ala Asn Lys Thr Ser Tyr Ile Asp Val
 65                  70                  75                  80

Leu Ile His Phe Glu Glu Gly Val Leu Tyr Glu Ile Asp Ser Lys Asn
                 85                  90                  95

Glu Ser Cys Lys Lys Glu Thr Leu Gln Phe Arg Lys His Leu Met Glu
                100                 105                 110

Ile Pro Val Asp Ala Thr His Glu Ser Glu Ser Tyr Met Gly Ser Pro
            115                 120                 125

Ser Leu Thr Glu Gln Gly Leu Arg Val Arg Val Trp Asn Gly Lys Phe
130                 135                 140

Pro Glu Leu His Ala His Tyr Ser Leu Ser Thr Thr Ser Cys Gly Cys
145                 150                 155                 160

Leu Thr Val Ser Gly Ser Tyr Tyr Gly Glu Lys Lys Asp Leu Phe Phe
                165                 170                 175

Ser Phe Phe Gly Val Glu Thr Glu Val Asp Asp Leu Gln Val Phe Ala
                180                 185                 190

Pro Pro Ala Tyr Cys Glu Gly Val Ser Phe Glu Ala Pro Asp Asp
            195                 200                 205

His Ser Phe Phe Asp Leu Phe His Asp
            210                 215

<210> SEQ ID NO 7
<211> LENGTH: 212
<212> TYPE: PRT
<213> ORGANISM: Clupea harengus

<400> SEQUENCE: 7

Met Arg Leu Thr Gly Leu Leu Cys Val Ala Leu Trp Ser Ala Ser Ala
  1               5                  10                  15

Val Val Leu Ala Glu His Gln Pro Cys Arg Pro Pro Gln Thr His
                 20                  25                  30

Gly Asn Leu Trp Val Thr Ala Ala Lys Gly Ala Pro Ala Ser Val Gly
             35                  40                  45

Glu Phe Asn Tyr Asp Ser Gln Ala Arg Lys Leu His Phe Lys Asp Asp
 50                  55                  60

Ala Leu His Val Asn Lys Thr Asp His Leu Glu Met Leu Ile Phe Phe
 65                  70                  75                  80

Glu Glu Gly Ile Phe Tyr Asp Ile Asp Ser His Asn Gln Ser Cys His
                 85                  90                  95

Lys Lys Thr Leu Gln Ser Thr Tyr His Cys Leu Glu Val Pro Pro Asn
                100                 105                 110

Ala Thr His Val Thr Glu Gly Tyr Leu Gly Ser Glu Phe Ile Gly Asp
            115                 120                 125

Gln Gly Val Arg Met Arg Lys Trp Arg Lys Arg Val Pro Glu Leu Asp
130                 135                 140

Gly Val Val Thr Val Ala Thr Thr Ser Cys Gly Cys Val Thr Leu Phe
145                 150                 155                 160

Ala Thr Leu Phe Thr Asp Ser Asn Asp Val Leu Val Phe Asn Phe Leu
                165                 170                 175

Asp Val Glu Met Lys Val Lys Asn Pro Leu Glu Val Phe Val Pro Pro
                180                 185                 190

Ser Tyr Cys Asp Gly Val Ala Leu Glu Glu Glu Gly Asp Thr Phe Phe
            195                 200                 205
```

Gly Leu Phe His
    210

<210> SEQ ID NO 8
<211> LENGTH: 24
<212> TYPE: DNA
<213> ORGANISM: Artificial sequence
<220> FEATURE:
<223> OTHER INFORMATION: Contains an Nde I restriction site

<400> SEQUENCE: 8
gcgcatatgg ccccgcgccc gtgc                                          24

<210> SEQ ID NO 9
<211> LENGTH: 29
<212> TYPE: DNA
<213> ORGANISM: Artificial sequence
<220> FEATURE:
<223> OTHER INFORMATION: Contains an Asp 718 restriction site

<400> SEQUENCE: 9
gcgggtacct caccaggagc agtcttcgc                                     29

<210> SEQ ID NO 10
<211> LENGTH: 51
<212> TYPE: DNA
<213> ORGANISM: Artificial sequence
<220> FEATURE:
<223> OTHER INFORMATION: Contains an XbaI restriction site and an
      efficient signal for initiation of translation in eukaryotic
      cells (Kozak, M., J. Mol. Biol. 196:947-950 (1987)

<400> SEQUENCE: 10
gatcgctcta gatccgccac catgccagga cgcgctcccc tccgcaccgt c            51

<210> SEQ ID NO 11
<211> LENGTH: 48
<212> TYPE: DNA
<213> ORGANISM: Artificial sequence
<220> FEATURE:
<223> OTHER INFORMATION: Contains an Asp 718 restriction site

<400> SEQUENCE: 11
gatcgcggta ccttatcacc aggagcagtc ttcgctcatc ttctccag                48

<210> SEQ ID NO 12
<211> LENGTH: 42
<212> TYPE: DNA
<213> ORGANISM: Artificial sequence
<220> FEATURE:
<223> OTHER INFORMATION: Contains an Asp 718 restriction site, a Kozak
      sequence, and an AUG start codon

<400> SEQUENCE: 12
gatcgcggta ccgccatcat gccaggacgc gctcccctcc gc                      42

<210> SEQ ID NO 13
<211> LENGTH: 32
<212> TYPE: DNA
<213> ORGANISM: Artificial sequence
<220> FEATURE:
<223> OTHER INFORMATION: Contains a BamHI restriction site

<400> SEQUENCE: 13
gatcgcggat cctcaccagg agcagtcttc gc                                 32

<210> SEQ ID NO 14
<211> LENGTH: 51
<212> TYPE: DNA
<213> ORGANISM: Artificial sequence
<220> FEATURE:
<223> OTHER INFORMATION: Contains an XbaI restriction site, a Kozak
      sequence, and an AUG start codon

<400> SEQUENCE: 14
gatcgctcta gatccgccac catgccagga cgcgctcccc tccgcaccgt c        51

<210> SEQ ID NO 15
<211> LENGTH: 506
<212> TYPE: DNA
<213> ORGANISM: Homo sapiens
<220> FEATURE:
<221> NAME/KEY: misc_feature
<222> LOCATION: (344)..(344)
<223> OTHER INFORMATION: n equals a, t, g or c
<220> FEATURE:
<221> NAME/KEY: misc_feature
<222> LOCATION: (354)..(354)
<223> OTHER INFORMATION: n equals a, t, g or c
<220> FEATURE:
<221> NAME/KEY: misc_feature
<222> LOCATION: (399)..(399)
<223> OTHER INFORMATION: n equals a, t, g or c
<220> FEATURE:
<221> NAME/KEY: misc_feature
<222> LOCATION: (416)..(416)
<223> OTHER INFORMATION: n equals a, t, g or c
<220> FEATURE:
<221> NAME/KEY: misc_feature
<222> LOCATION: (425)..(425)
<223> OTHER INFORMATION: n equals a, t, g or c
<220> FEATURE:
<221> NAME/KEY: misc_feature
<222> LOCATION: (465)..(465)
<223> OTHER INFORMATION: n equals a, t, g or c
<220> FEATURE:
<221> NAME/KEY: misc_feature
<222> LOCATION: (490)..(490)
<223> OTHER INFORMATION: n equals a, t, g or c
<220> FEATURE:
<221> NAME/KEY: misc_feature
<222> LOCATION: (501)..(502)
<223> OTHER INFORMATION: n equals a, t, g or c

<400> SEQUENCE: 15
aattcggcac gagcacaaga gttgctccca agcctggatg agttgcacct tgcatcttga    60
gcatgcattt ctcacaataa ttattaagct gtgtgataat ttctgctttc aggacactca   120
tccattatct tggctgtgag ctccttgggt acgggtacct tgtatgttta attttatatc   180
cctagcacaa agcaagtgcc tggcacatag tcagtgccct aagtatttgt agagtgaaga   240
atgccagcct ctcttgtccc tggtttcctt atgtgttgaa tgtggttgag tttgtccatt   300
gctagggaga gacttccagt aataaaattt actattctag atgntctact gtantgttta   360
tctgcccatt tatcttctta gtaccagggg aaagtgtgnc acccttttt aatggnaaca    420 acttnttacc taaggttacc cttttaacaa attaatgcat taagnatctt ggaatgtggc   480
ttgaaaaaan gggaactggt nnaggg                                        506

<210> SEQ ID NO 16
<211> LENGTH: 409
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n equals a, t, g or c

```
<220> FEATURE:
<221> NAME/KEY: misc_feature
<222> LOCATION: (271)..(271)
<223> OTHER INFORMATION: n equals a, t, g or c
<220> FEATURE:
<221> NAME/KEY: misc_feature
<222> LOCATION: (273)..(273)
<223> OTHER INFORMATION: n equals a, t, g or c
<220> FEATURE:
<221> NAME/KEY: misc_feature
<222> LOCATION: (284)..(284)
<223> OTHER INFORMATION: n equals a, t, g or c
<220> FEATURE:
<221> NAME/KEY: misc_feature
<222> LOCATION: (301)..(301)
<223> OTHER INFORMATION: n equals a, t, g or c
<220> FEATURE:
<221> NAME/KEY: misc_feature
<222> LOCATION: (317)..(317)
<223> OTHER INFORMATION: n equals a, t, g or c
<220> FEATURE:
<221> NAME/KEY: misc_feature
<222> LOCATION: (319)..(319)
<223> OTHER INFORMATION: n equals a, t, g or c
<220> FEATURE:
<221> NAME/KEY: misc_feature
<222> LOCATION: (328)..(328)
<223> OTHER INFORMATION: n equals a, t, g or c
<220> FEATURE:
<221> NAME/KEY: misc_feature
<222> LOCATION: (339)..(339)
<223> OTHER INFORMATION: n equals a, t, g or c
<220> FEATURE:
<221> NAME/KEY: misc_feature
<222> LOCATION: (348)..(348)
<223> OTHER INFORMATION: n equals a, t, g or c
<220> FEATURE:
<221> NAME/KEY: misc_feature
<222> LOCATION: (357)..(357)
<223> OTHER INFORMATION: n equals a, t, g or c
<220> FEATURE:
<221> NAME/KEY: misc_feature
<222> LOCATION: (364)..(364)
<223> OTHER INFORMATION: n equals a, t, g or c
<220> FEATURE:
<221> NAME/KEY: misc_feature
<222> LOCATION: (370)..(370)
<223> OTHER INFORMATION: n equals a, t, g or c
<220> FEATURE:
<221> NAME/KEY: misc_feature
<222> LOCATION: (375)..(375)
<223> OTHER INFORMATION: n equals a, t, g or c
<220> FEATURE:
<221> NAME/KEY: misc_feature
<222> LOCATION: (383)..(383)
<223> OTHER INFORMATION: n equals a, t, g or c
<220> FEATURE:
<221> NAME/KEY: misc_feature
<222> LOCATION: (403)..(403)
<223> OTHER INFORMATION: n equals a, t, g or c

<400> SEQUENCE: 16
aattcggcac gaggcagttt agagaatcct aatgtctaca ctggcatagc acgagccatg    60
taagcttctt ttttttctat gcaagagtat tgatgtatgt nctgaatctt cacagacttg   120
tcaatacaca ggcagtattc taaaatagca ctgaacaggg agtcaggaga ctattgtctc   180
ctaaacccag gactagagtt ccctcgtact gtcactcctt tggtcattaa atgcactggg   240
cttgcccgca ctttggcctt cctagaacgt ngnttcaaaa cctnttttggt ctgactttttg  300 naattccctt ccagggnang tcattcanaa ggggttttnc caagcctngg tgggttnaac   360
ctgnaatttn gggangtttt ttnaaaaaat tttaagggggg ggnaaattt              409

<210> SEQ ID NO 17
```

```
<211> LENGTH: 310
<212> TYPE: DNA
<213> ORGANISM: Homo sapiens
<220> FEATURE:
<221> NAME/KEY: misc_feature
<222> LOCATION: (252)
<223> OTHER INFORMATION: n equals a, t, g or c

<400> SEQUENCE: 17
gagaagtttg ccttggcagc aagtatttat tgttgacatt attcagaatt agtgataata      60
aaaagcagag tgattttggt caattttatt attaattctt aaattccctg cagagaatgc     120
cccctttatt gctgcaccag ggtgggcatt gctcccactg agccctactc caccctgtcc     180
ctgcactccc ttggttgcca aaaaatgat aacttaaatc ccttccagac ttaagaattt      240
tatgggcatg gnccaattga tattaaacat ttagaaggga atgaaagctt aaatagggag     300
taattattcc                                                            310

<210> SEQ ID NO 18
<211> LENGTH: 469
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n equals a, t, g or c
<220> FEATURE:
<221> NAME/KEY: misc_feature
<222> LOCATION: (19)..(19)
<223> OTHER INFORMATION: n equals a, t, g or c
<220> FEATURE:
<221> NAME/KEY: misc_feature
<222> LOCATION: (265)..(265)
<223> OTHER INFORMATION: n equals a, t, g or c
<220> FEATURE:
<221> NAME/KEY: misc_feature
<222> LOCATION: (276)..(276)
<223> OTHER INFORMATION: n equals a, t, g or c
<220> FEATURE:
<221> NAME/KEY: misc_feature
<222> LOCATION: (287)..(287)
<223> OTHER INFORMATION: n equals a, t, g or c
<220> FEATURE:
<221> NAME/KEY: misc_feature
<222> LOCATION: (372)..(372)
<223> OTHER INFORMATION: n equals a, t, g or c
<220> FEATURE:
<221> NAME/KEY: misc_feature
<222> LOCATION: (383)..(384)
<223> OTHER INFORMATION: n equals a, t, g or c
<220> FEATURE:
<221> NAME/KEY: misc_feature
<222> LOCATION: (397)..(397)
<223> OTHER INFORMATION: n equals a, t, g or c
<220> FEATURE:
<221> NAME/KEY: misc_feature
<222> LOCATION: (401)..(401)
<223> OTHER INFORMATION: n equals a, t, g or c
<220> FEATURE:
<221> NAME/KEY: misc_feature
<222> LOCATION: (410)..(410)
<223> OTHER INFORMATION: n equals a, t, g or c
<220> FEATURE:
<221> NAME/KEY: misc_feature
<222> LOCATION: (414)..(414)
<223> OTHER INFORMATION: n equals a, t, g or c
<220> FEATURE:
<221> NAME/KEY: misc_feature
<222> LOCATION: (417)..(417)
<223> OTHER INFORMATION: n equals a, t, g or c
<220> FEATURE:
<221> NAME/KEY: misc_feature
<222> LOCATION: (439)..(440)
<223> OTHER INFORMATION: n equals a, t, g or c
```

```
<220> FEATURE:
<221> NAME/KEY: misc_difference
<222> LOCATION: (454)..(454)
<223> OTHER INFORMATION: n equals a, t, g or c

<400> SEQUENCE: 18
aattcggcan agacggcang agacatgaaa cactttattt attacagcat tgttttaact      60
cccttataac aagattatc catatttatt gcaaaagcaa caatatcaaa gaatgcttta      120
aaatgcaatt gaaatttgtt taatatagat aaactataag taataagatt gttttcatta    180
taatataggt gtcacacatt tctcctggta actaaggaaa gataaatggg cagataaaac    240
ataacagtag aagcatctag gattngttaa tttttnttac tgggagngct cttccctagg    300
cattttacca acttcaacca ctttcaacac atagggaac ccagggccca gggggggctg     360 ggcattttc antttggggg ttnnttgggg cccggcnttt ntgcccgggn ttgnttntgg     420
gctgggggtt taaattttnn ccttccaggg cccnttcccc gggggttt                 469

<210> SEQ ID NO 19
<211> LENGTH: 382
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n equals a, t, g or c
<220> FEATURE:
<221> NAME/KEY: misc_feature
<222> LOCATION: (61)..(63)
<223> OTHER INFORMATION: n equals a, t, g or c
<220> FEATURE:
<221> NAME/KEY: misc_feature
<222> LOCATION: (268)..(268)
<223> OTHER INFORMATION: n equals a, t, g or c
<220> FEATURE:
<221> NAME/KEY: misc_feature
<222> LOCATION: (280)..(280)
<223> OTHER INFORMATION: n equals a, t, g or c
<220> FEATURE:
<221> NAME/KEY: misc_feature
<222> LOCATION: (336)..(336)
<223> OTHER INFORMATION: n equals a, t, g or c
<220> FEATURE:
<221> NAME/KEY: misc_feature
<222> LOCATION: (348)..(348)
<223> OTHER INFORMATION: n equals a, t, g or c
<220> FEATURE:
<221> NAME/KEY: misc_feature
<222> LOCATION: (355)..(355)
<223> OTHER INFORMATION: n equals a, t, g or c
<220> FEATURE:
<221> NAME/KEY: misc_feature
<222> LOCATION: (367)..(367)
<223> OTHER INFORMATION: n equals a, t, g or c
<220> FEATURE:
<221> NAME/KEY: misc_feature
<222> LOCATION: (381)..(381)
<223> OTHER INFORMATION: n equals a, t, g or c

<400> SEQUENCE: 19
ggcacgaggg aaaaccgaag cggcagaagg cagtggcagc aggcagtggc agnaggcagt    60
nnnccaggct ggacgagagg aaggcgctga tccoctgcaa gagaattatt tggatatatt   120
ttggtgtata aggatggagt gatgtttcaa attgaccaag ccaccaagca gtgctcaaag   180
ccctgacaca gccctgggat cctcttgaca ttcctcaaaa ctccacctttt gaagaccagt  240 actccattgg ggggcctcag gagccagtc accgtccagn agtggtcgga cagaaagtca   300
gcttaggtcc tatgaaacct gggttgggca tttatnacag ttcaaggntt ggttnttctg   360
ttccagnaaa ccttttacct nt                                             382
```

```
<210> SEQ ID NO 20
<211> LENGTH: 465
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n equals a, t, g or c
<220> FEATURE:
<221> NAME/KEY: misc_feature
<222> LOCATION: (163)..(164)
<223> OTHER INFORMATION: n equals a, t, g or c
<220> FEATURE:
<221> NAME/KEY: misc_feature
<222> LOCATION: (294)..(294)
<223> OTHER INFORMATION: n equals a, t, g or c
<220> FEATURE:
<221> NAME/KEY: misc_feature
<222> LOCATION: (337)..(337)
<223> OTHER INFORMATION: n equals a, t, g or c
<220> FEATURE:
<221> NAME/KEY: misc_feature
<222> LOCATION: (355)..(355)
<223> OTHER INFORMATION: n equals a, t, g or c
<220> FEATURE:
<221> NAME/KEY: misc_feature
<222> LOCATION: (361)..(361)
<223> OTHER INFORMATION: n equals a, t, g or c
<220> FEATURE:
<221> NAME/KEY: misc_feature
<222> LOCATION: (401)..(401)
<223> OTHER INFORMATION: n equals a, t, g or c
<220> FEATURE:
<221> NAME/KEY: misc_feature
<222> LOCATION: (414)..(414)
<223> OTHER INFORMATION: n equals a, t, g or c
<220> FEATURE:
<221> NAME/KEY: misc_feature
<222> LOCATION: (425)..(425)
<223> OTHER INFORMATION: n equals a, t, g or c
<220> FEATURE:
<221> NAME/KEY: misc_feature
<222> LOCATION: (442)..(442)
<223> OTHER INFORMATION: n equals a, t, g or c
<220> FEATURE:
<221> NAME/KEY: misc_feature
<222> LOCATION: (461)..(461)
<223> OTHER INFORMATION: n equals a, t, g or c

<400> SEQUENCE: 20
gaattcggca gagncttata gtttatctat attaaacaaa tttaattgca tttaaagcat      60
tctttgatat tgttgctttt gcaatgaaat atggataatc ttggttataa gggagttaaa     120
acaatgctgt aataaataaa gtgtttcatg tgatcaaaat cannntttgtt atcctctctc    180 aaaagcctgc tctccctctt accttcccta aactccagtg tccatttgcc aaggccagaa     240
gcttccaagt cattcttgga tccatttgtc tccctcagtc ctcactgggc agtncaatat    300
cccgagtcct attcaaaata gcttctttaa aactttntgc ctgtttcttc cactnccttg    360
nccctcaggc cagggcccct gctgggaagg gggctggcat ntttcctgtt cagncctggg    420
gtttnccatg ggtggactgg gngtgacgga ggccacctgg nggtt                    465
```